(12) United States Patent
Carney et al.

(10) Patent No.: US 11,931,589 B2
(45) Date of Patent: Mar. 19, 2024

(54) LOW POWER WIRELESS COMMUNICATION

(71) Applicant: Medtronic, Inc., Minneapolis, MN (US)

(72) Inventors: James K. Carney, Roseville, MN (US); Saul E. Greenhut, Denver, CO (US); Jonathan L. Kuhn, Ham Lake, MN (US); James D. Reinke, Maple Grove, MN (US); David J. Peichel, Minneapolis, MN (US); James W. Busacker, St Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 617 days.

(21) Appl. No.: 17/012,745

(22) Filed: Sep. 4, 2020

(65) Prior Publication Data
US 2020/0398064 A1 Dec. 24, 2020

Related U.S. Application Data

(62) Division of application No. 15/484,430, filed on Apr. 11, 2017, now Pat. No. 10,773,088.

(51) Int. Cl.
*A61N 1/372* (2006.01)
*A61B 5/00* (2006.01)
(Continued)

(52) U.S. Cl.
CPC ........ *A61N 1/37288* (2013.01); *A61B 5/0031* (2013.01); *A61B 5/29* (2021.01);
(Continued)

(58) Field of Classification Search
CPC .... A61N 1/37252; A61N 1/362; A61N 1/025; A61N 1/36; A61N 1/3704;
(Continued)

(56) References Cited

U.S. PATENT DOCUMENTS

| | | |
|---|---|---|
| 4,987,897 A | 1/1991 | Funke |
| 5,113,859 A | 5/1992 | Funke |

(Continued)

FOREIGN PATENT DOCUMENTS

| | | |
|---|---|---|
| CN | 105102060 A | 11/2015 |
| CN | 106132482 A | 11/2016 |

(Continued)

OTHER PUBLICATIONS

US 8,886,318 B2, 11/2014, Jacobson et al. (withdrawn)

(Continued)

*Primary Examiner* — Deborah L Malamud
(74) *Attorney, Agent, or Firm* — Shumaker & Sieffert, P.A.

(57) ABSTRACT

Systems, devices, and techniques for establishing communication between two medical devices are described. In one example, an implantable medical device comprises communication circuitry, therapy delivery circuitry, and processing circuitry configured to initiate a communication window during which the implantable second medical device is capable of receiving the information related to a cardiac event detected by a first medical device, the communication window being one of a plurality of communication windows defined by a communication schedule that corresponds to a transmission schedule in which the first medical device is configured to transmit the information, control the communication circuitry to receive, from the first medical device, the information related to the cardiac event that is indicative of a timing of the cardiac event with respect to a timing of the communication window, schedule and control delivery of a therapy according to the information related to the cardiac event.

25 Claims, 15 Drawing Sheets

(51) Int. Cl.
*A61B 5/29* (2021.01)
*A61N 1/365* (2006.01)
*A61N 1/39* (2006.01)
*H04B 13/00* (2006.01)
*A61N 1/362* (2006.01)
*A61N 1/368* (2006.01)
*A61N 1/375* (2006.01)

(52) U.S. Cl.
CPC ............ *A61B 5/4836* (2013.01); *A61N 1/365* (2013.01); *A61N 1/37276* (2013.01); *A61N 1/3925* (2013.01); *A61N 1/3962* (2013.01); *H04B 13/005* (2013.01); *A61B 5/0024* (2013.01); *A61B 5/7282* (2013.01); *A61B 2560/0209* (2013.01); *A61N 1/3627* (2013.01); *A61N 1/3684* (2013.01); *A61N 1/37205* (2013.01); *A61N 1/3756* (2013.01)

(58) Field of Classification Search
CPC ........ A61N 1/37235; A61N 1/05; A61N 1/08; A61N 1/3702; A61N 1/37288; A61N 1/39622; A61N 1/37; A61N 1/37211; A61N 1/3603; A61B 5/0031; A61B 5/686; A61B 5/4836; A61B 5/7282; A61B 5/0245; A61B 5/0402; A61B 5/0452; A61B 5/04012; A61B 5/7285; A61B 5/0006; A61B 5/0015; A61B 5/0084; A61B 5/05; A61B 5/6847; A61B 5/6867; G06F 19/00; G06F 19/3418; H04L 2209/88
See application file for complete search history.

(56) References Cited

U.S. PATENT DOCUMENTS

| | | | |
|---|---|---|---|
| 5,117,824 A | 6/1992 | Keimel et al. | |
| 5,312,445 A | 5/1994 | Nappholz et al. | |
| 5,545,186 A | 8/1996 | Olson et al. | |
| 5,755,736 A | 5/1998 | Gillberg et al. | |
| 6,459,928 B2 | 10/2002 | Mika et al. | |
| 6,890,294 B2 | 5/2005 | Niwa et al. | |
| 7,945,333 B2 | 5/2011 | Jacobson | |
| 8,457,742 B2 | 6/2013 | Jacobson | |
| 8,547,248 B2 | 10/2013 | Zdeblick et al. | |
| 8,744,572 B1 | 6/2014 | Greenhut et al. | |
| 8,788,053 B2 | 7/2014 | Jacobson | |
| 8,798,745 B2 | 8/2014 | Jacobson | |
| 8,923,963 B2 | 12/2014 | Bonner et al. | |
| 9,072,914 B2 | 7/2015 | Greenhut et al. | |
| 9,168,380 B1 * | 10/2015 | Greenhut | A61N 1/37288 |
| 9,492,677 B2 | 11/2016 | Greenhut et al. | |
| 9,636,511 B2 | 5/2017 | Carney et al. | |
| 9,918,638 B2 | 3/2018 | Cinbis et al. | |
| 2007/0088398 A1 | 4/2007 | Jacobson | |
| 2007/0239230 A1 | 10/2007 | Giftakis et al. | |
| 2012/0109236 A1 | 5/2012 | Jacobson et al. | |
| 2013/0027186 A1 | 1/2013 | Cinbis et al. | |
| 2013/0231710 A1 | 9/2013 | Jacobson | |
| 2014/0121120 A1 | 5/2014 | Chen et al. | |
| 2014/0121720 A1 | 5/2014 | Bonner et al. | |
| 2014/0309706 A1 | 10/2014 | Jacobson | |
| 2015/0142069 A1 | 5/2015 | Sambelashvili | |
| 2015/0142070 A1 | 5/2015 | Sambelashvili | |
| 2015/0196756 A1 | 7/2015 | Stahmann et al. | |
| 2015/0224320 A1 | 8/2015 | Stahmann | |
| 2015/0321011 A1 | 11/2015 | Carney et al. | |
| 2015/0321012 A1 | 11/2015 | Cinbis et al. | |
| 2015/0321016 A1 | 11/2015 | Richard | |
| 2016/0121128 A1 | 5/2016 | Fishler et al. | |
| 2016/0121129 A1 | 5/2016 | Persson et al. | |
| 2016/0213939 A1 | 7/2016 | Carney et al. | |
| 2018/0021583 A1 | 1/2018 | Ciciarelli et al. | |

FOREIGN PATENT DOCUMENTS

| | | |
|---|---|---|
| WO | 2011093916 | 8/2011 |
| WO | 2015153463 A1 | 10/2015 |

OTHER PUBLICATIONS

First Office Action and Search Report, and translation thereof, from counterpart Chinese Application No. 201880024686.4 dated Jan. 19, 2023, 16 pp.

(PCT/US2018/027010)Notification of Transmittal of the International Search Report and the Written Opinion of the International Searching Authority, dated Aug. 30, 2018, 15 pages.

Carney et al., "Low Power Wireless Communication", Invitation to Pay Additional Fees, (PCT/US2018/027010), dated Jul. 6, 2018, 7 pages.

Office Action, and translation thereof, from counterpart Application No. 201880024686.4 dated Aug. 28, 2023, 17 pp.

\* cited by examiner

LOW POWER WIRELESS COMMUNICATION

CROSS-REFERENCE TO RELATED APPLICATIONS

The present application is a Continuation Application which claims that benefit of and priority to U.S. patent application Ser. No. 15/484,430, filed on Apr. 11, 2017, the entire content of which is incorporated herein by reference.

TECHNICAL FIELD

This disclosure relates generally to medical devices and, more particularly, to communication techniques between medical devices.

BACKGROUND

An implantable pacemaker may deliver pacing pulses to a patient's heart and monitor conditions of the patient's heart. The implantable pacemaker may comprise a pulse generator and one or more electrical leads. The pulse generator may be implanted in a small pocket in the patient's chest, in some examples. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) where electrodes at the distal ends of the electrical leads connect to the target site. The pulse generator may provide electrical stimulation to the target site and/or monitor cardiac electrical activity at the target site via the electrodes.

In some examples, a leadless pacemaker may be used to sense electrical activity and/or deliver therapeutic signals to the heart. The leadless pacemaker may include one or more electrodes on its outer housing to deliver therapeutic electrical signals and/or sense intrinsic depolarizations of the heart. The leadless pacemaker may be positioned within or outside of the heart and, in some examples, may be anchored to a wall of the heart via a fixation mechanism.

SUMMARY

Systems, devices, and techniques for managing communication between two or more medical devices are described. For example, the two medical devices may utilize a transmission schedule that defines a plurality of transmission windows during which one of the medical devices (e.g., a master device) can send information (e.g., a control signal that indicates a time for when a next therapy should be delivered to a patient or a signal indicative of a timing between a detected cardiac event and the transmission window). The other medical device (e.g., an implantable medical device) may periodically enable, or turn on, communication circuitry during communication windows defined by a communication schedule. By aligning, or synchronizing, the transmission schedule and the communication schedule in time, the implantable medical device may "listen" (e.g., enable or turn on communication circuitry) for information (such as control signals or other signals) only during the communication windows in order to limit power consumption. In this manner, an implantable medical device may be constructed with a smaller battery, and of a smaller size, and/or provide a longer operational life by not powering communication circuitry outside of the scheduled communication window.

In one example, this disclosure is directed to a method including detecting, by a first medical device, a cardiac event of a patient, determining, by the first medical device, a timing of a transmission window, the transmission window being one transmission window of a plurality of transmission windows defined by a transmission schedule, generating, by the first medical device and based on a timing of the cardiac event with respect to the timing of the transmission window, information related to the cardiac event, and transmitting, by the first medical device and during the transmission window defined by the transmission schedule, the information related to the cardiac event to an implantable second medical device that is distinct from the first medical device.

In another example, this disclosure is directed to a method that includes initiating, by an implantable second medical device, a communication window during which the implantable second medical device is capable of receiving information related to a cardiac event from a first medical device, the communication window being one communication window of a plurality of communication windows defined by a communication schedule that corresponds to a transmission schedule defining a plurality of transmission windows in which the first medical device is configured to transmit the information related to the cardiac event, wherein the implantable second medical device is not capable of receiving the information related to the cardiac event between the plurality of communication windows, receiving, by the implantable second medical device and from the first medical device during the communication window, the information related to the cardiac event that is indicative of a timing of the cardiac event with respect to a timing of the communication window, scheduling, by the implantable second medical device, delivery of a therapy according to the information related to the cardiac event, and delivering, by the implantable second medical device, the therapy to a patient.

In a further example, this disclosure is directed to first medical device comprising sensing circuitry configured to detect a cardiac event of a patient, processing circuitry configured to determine a timing of a transmission window, the transmission window being one transmission window of a plurality of transmission windows defined by a transmission schedule, and generating, by the first medical device and based on a timing of the cardiac event with respect to the timing of the transmission window, information related to the cardiac event, and communication circuitry configured to transmit, during the transmission window defined by the transmission schedule, the information related to the cardiac event to an implantable second medical device that is distinct from the first medical device In a further example, this disclosure is directed to implantable second medical device comprising communication circuitry configured to wirelessly receive information related to a cardiac event from a first medical device, therapy delivery circuitry configured to deliver therapy to a patient, and processing circuitry configured to initiate a communication window during which the implantable second medical device is capable of receiving the information related to the cardiac event from the first medical device, the communication window being one communication window of a plurality of communication windows defined by a communication schedule that corresponds to a transmission schedule defining a plurality of transmission windows in which the first medical device is configured to transmit the information related to the cardiac event, wherein the implantable second medical device is not capable of receiving the information related to the cardiac event between the plurality of communication windows, control the communication circuitry to receive, from the first medical device during the communication window, the information related to the cardiac event that is indicative of a timing of the cardiac event with respect to a timing of the communication window, schedule delivery of a therapy according to the information related to the cardiac event, and control the therapy delivery circuitry to deliver the therapy to the patient.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Figure 1:
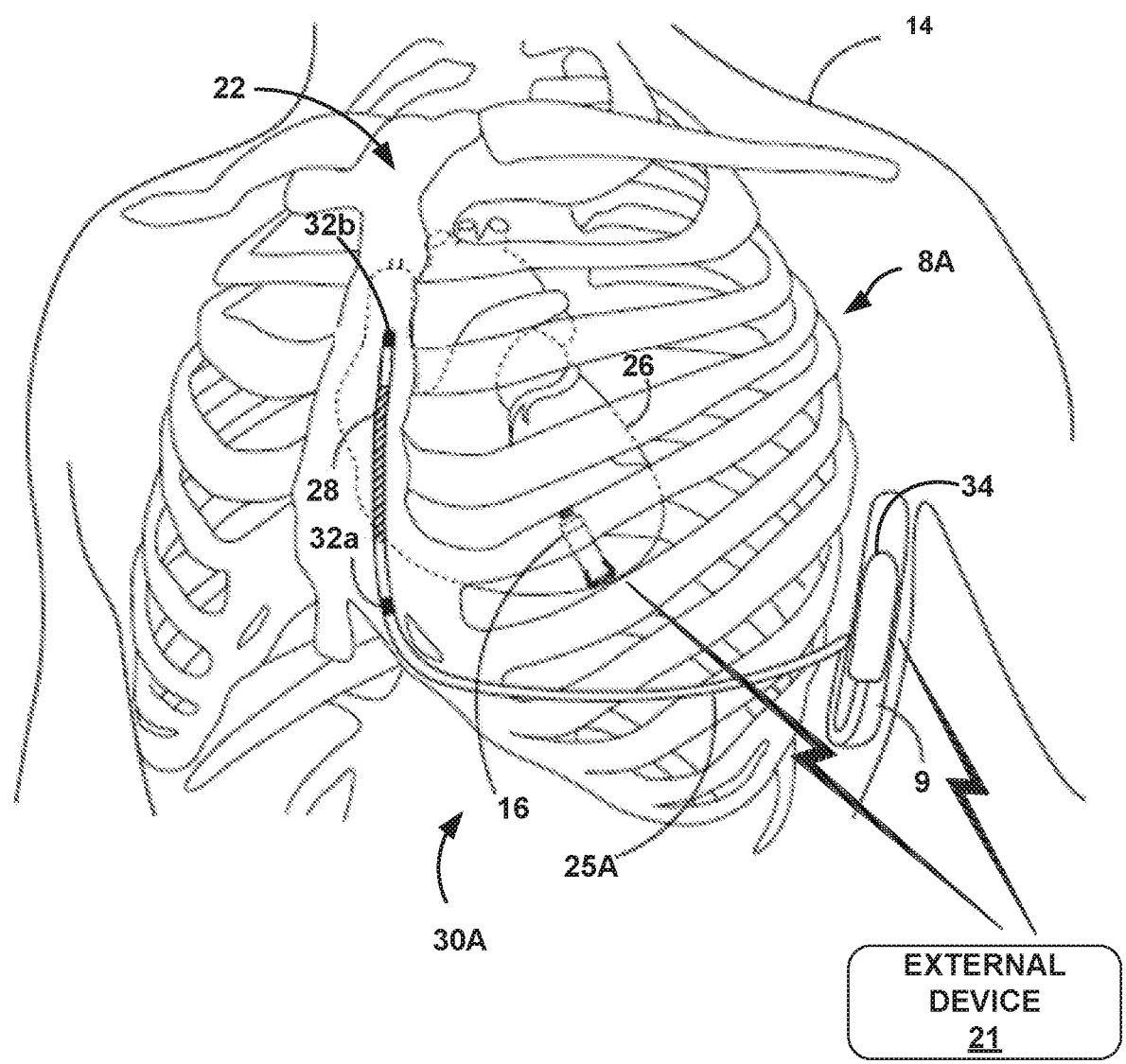
FIG. 1 is an example front view of a patient implanted with an example medical device system that includes an extracardiovascular ICD system and a pacing device (PD) implanted within a cardiac chamber of the patient in accordance with one or more aspects of the present disclosure.

In general, this disclosure describes subject matter relating to systems, devices, and techniques for managing communication between two or more medical devices. Medical devices may need to communicate during operation. The communication may be two-way communication between the medical devices or one-way communication where one device transmits information and another device receives information. In addition, the devices may operate in different modes, such as two-way communication modes or one-way communication modes, depending on the operational requirements of the device. Communication may be desired for transferring and receiving sensed data, operational commands, error messages, or any other information related to the operation of the devices and/or the status of the patient to which the devices are associated.

In one example, a first medical device (e.g., a master device) may be configured to sense a physiological event and determine information (e.g., a timing of the physiological event and/or a timing of when the type of therapy needs to be delivered based on that detected physiological event). However, a second medical device (e.g., a slave device) may contain the therapy delivery components and/or be positioned appropriately with respect to the patient to deliver the therapy. If the two medical devices are not connected via a physical connection (e.g., a wire or other conductor), the medical devices must transfer data via wireless communication such that the first medical device can send information (e.g., a control signal) and the second medical device can wirelessly receive the information (e.g., a control signal). Since the second medical device will not know when the first medical device will detect the physiological event or send the information related to the detection of the physiological event, the second medical device will "listen" or enable wireless communication for most, if not all, of the time of operation in order to avoid missing the transmitted information from the first medical device. Maintaining wireless communication capability consumes battery power, even if no information is being received during this time. This consumption of power can reduce the operational life of battery and/or the operational life of the second medical device. In order to maintain wireless communication capability for long durations of time in anticipation of signals from the first medical device, the second medical device may include a rechargeable battery that requires periodic recharging and/or a larger battery with greater capacity to support this type of wireless communication regime.

As described herein, medical devices may utilize wireless communication regimes that reduce the amount of time, or the duty cycle, that a medical device uses to enable wireless communication for detecting information such as signals or data from another device. For example, the medical devices can synchronize schedules for transmitting and receiving data and then each medical device can independently maintain the respective schedule. In effect, the second medical device can anticipate when any signal would be transmitted from the first medical device and disable the communication circuitry outside of this anticipated window. Consequently, medical devices configured to utilize the wireless communication regimes described herein may not need to include a rechargeable battery that requires periodic recharging and/or a larger battery with greater capacity.

In one example, the communication regime may include a transmission schedule defining a plurality of transmission windows during which signals can be transmitted from a first medical device (e.g., an implantable medical device or an external device) to a second medical device (e.g., an implantable medical device) and a communication schedule defining a plurality of communication windows during which the second medical device enables wireless communication for receiving signals from the first medical device. The communication windows are synchronized to align in time with respective transmission windows such that signals sent during the transmission windows would be received by the second medical device during the corresponding communication windows. In some examples, the transmission windows may be specific points in time for which a signal can be sent, and the communication windows may define some duration of time during which the second medical device is capable of receiving or detecting the transmitted signal.

By synchronizing the communication windows with the respective transmission windows, both the first medical device and the second medical device can reduce the amount of time, or the duty cycle, during which communication circuitry of each device is powered up and active. This reduced duty cycle can reduce the amount of power required by the devices to maintain communication. For example, the duty cycle for the communication windows of the second medical device can be less than 2 percent, or even less than 1 percent, using the techniques disclosed herein while effectively receiving any signal that would be sent from the first medical device. The duty cycle of the communication windows may be an average duty cycle for the communication windows with respect to the total amount of time of the communication schedule between delivered therapies. The second medical device may synchronize its communication schedule to a synchronization signal sent by the first medical device by shifting the communication schedule forward or backward in time according to the timing of the received synchronization signal. If the second medical device misses a predetermined number of expected signals (e.g., information such as control signals and/or synchronization signals), the second medical device may increase the duration of the communication windows and/or increase the rate of the communication windows until the expected signals are again received.

The first medical device may be configured to transmit information to the second medical device that is related to a detected physiological event. As generally described herein, the information may be or include a control signal that indicates a time for when a next therapy should be delivered to a patient by the second medical device. In this manner, the control signal may specify the time to deliver therapy with respect to the timing of the delivered control signal. Since the first medical device generates the control signal to include the timing of the therapy, the second medical device is not tasked with performing any analysis of the detected cardiac event or determination of when to deliver the therapy. However, the information transmitted by the first medical device may provide alternative types of data. For example, the transmitted information may include timing information that indicates when the first medical device detected the physiological event (e.g., a cardiac event such as a P-wave). The timing information may indicate when the physiological event was detected based on the timing of the transmission window. The second medical device may then analyze the timing of the detected event and determine when to deliver the therapy based on the timing of the detected event. In this manner, the second medical device may provide additional processing capabilities for analyzing the timing of the event and determining when to deliver therapy. In any event, the first medical device may transmit any information related to the detected physiological event during the scheduled transmission window such that the second medical device can receive the information during the corresponding communication window of the communication schedule.

Since the transmission rate of the first medical device is limited to the rate of the transmission windows, the control signal sent during a transmission window may not merely include a command to "immediately delivery therapy." In other words, the transmission windows may not correspond to the times at which therapy should be delivered by the second medical device. Instead, the control signal may indicate an amount of time, or delay, between the time that the control signal is transmitted (and consequently received) and the time at which therapy (e.g., a pacing pulse to an atrium or a ventricle of a heart) is to be delivered by the second medical device in the future. For example, if the transmission window occurs every 50 milliseconds (ms), but the therapy is to be delivered 40 ms after a transmission window in which the control signal is sent, the first medical device may generate the control signal to indicate that the second medical device is to deliver therapy 40 ms after the control signal is received by the second medical device. In some examples, the second medical device may further reduce communication circuitry power consumption by keeping the communication circuitry disabled for one or more communication windows of the communication schedule (e.g., blanking windows) during which no control signals are expected to be transmitted. These and other examples are described in further detail herein.

FIG. 1 is a front view of an example medical device system 8A that includes an extracardiovascular ICD system 30A and PD 16 implanted within a patient. In the example of FIG. 1, extracardiovascular ICD system 30A includes ICD 9 coupled to a cardiac defibrillation lead 25A, which extends subcutaneously above the ribcage from ICD 9. In the example of FIG. 1, ICD 9 and PD 16 are examples of implantable medical devices. In the illustrated example, defibrillation lead 25A extends toward a center of the torso of patient 14, bends or turns near the center of the torso, and extends subcutaneously superior above the ribcage and/or sternum 22. Defibrillation lead 25A may be offset laterally to the left or the right of sternum 22 or located over sternum 22. Defibrillation lead 25A may extend substantially parallel to sternum 22 or be angled lateral from the sternum at either the proximal or distal end.

Defibrillation lead 25A includes an insulative lead body having a proximal end that includes a connector 34 configured to be connected to ICD 9 and a distal portion that includes one or more electrodes. Defibrillation lead 25A also includes one or more conductors that form an electrically conductive path within the lead body and interconnect the electrical connector and respective ones of the electrodes. In the example of FIG. 1, defibrillation lead 25A includes a single defibrillation electrode 28 toward the distal portion of defibrillation lead 25A, e.g., toward the portion of defibrillation lead 25A extending along sternum 22. Defibrillation lead 25A is placed along sternum such that a therapy vector between defibrillation electrode 28 and a housing electrode formed by or on ICD 9 (or other second electrode of the therapy vector) is substantially across a ventricle of heart 26.

Figure 2A:
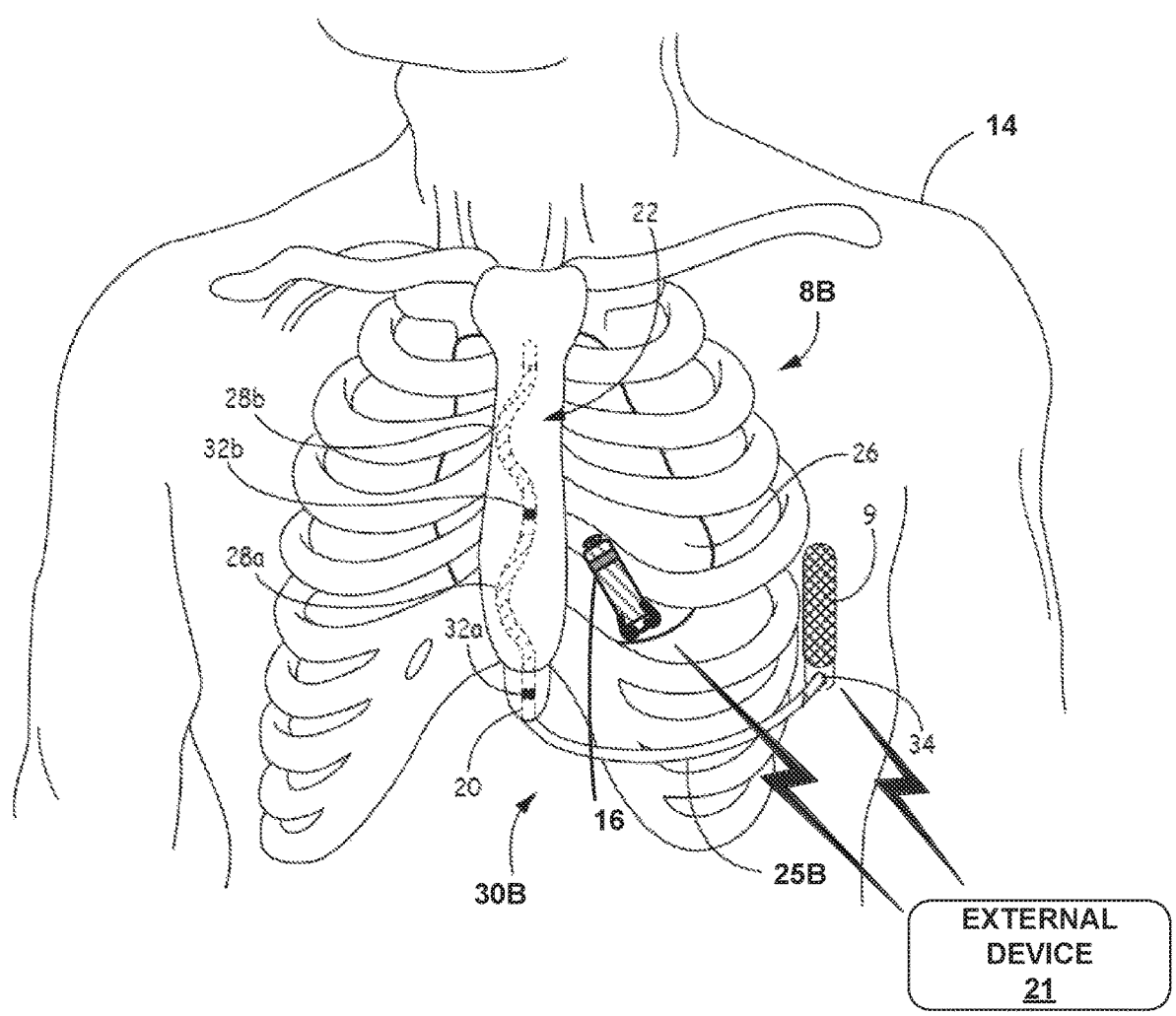
FIG. 2A is an example front view of a patient implanted with another example medical device system that includes an extracardiovascular ICD system and a pacing device (PD) implanted within a cardiac chamber of the patient in accordance with one or more aspects of the present disclosure.
Figure 2B:
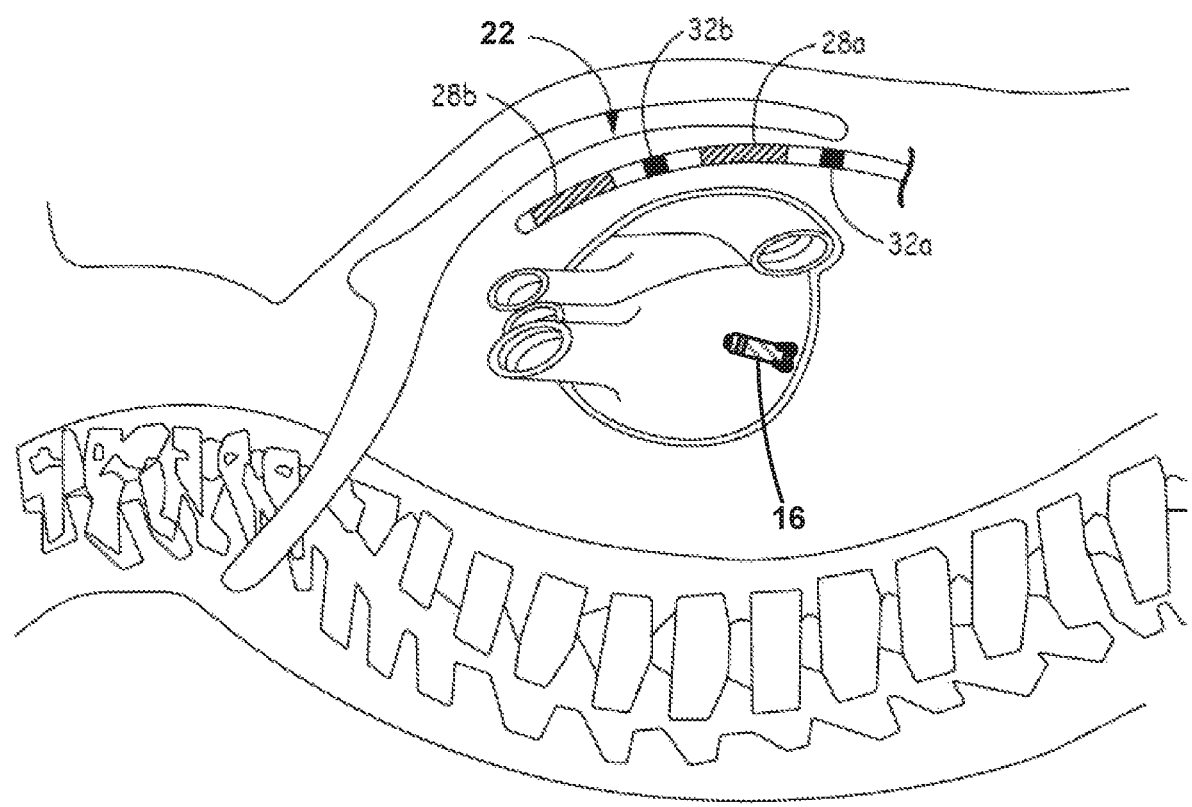
FIG. 2B is an example side view of a patient implanted with the example medical device system of FIG. 2A in accordance with one or more aspects of the present disclosure.
Figure 2C:
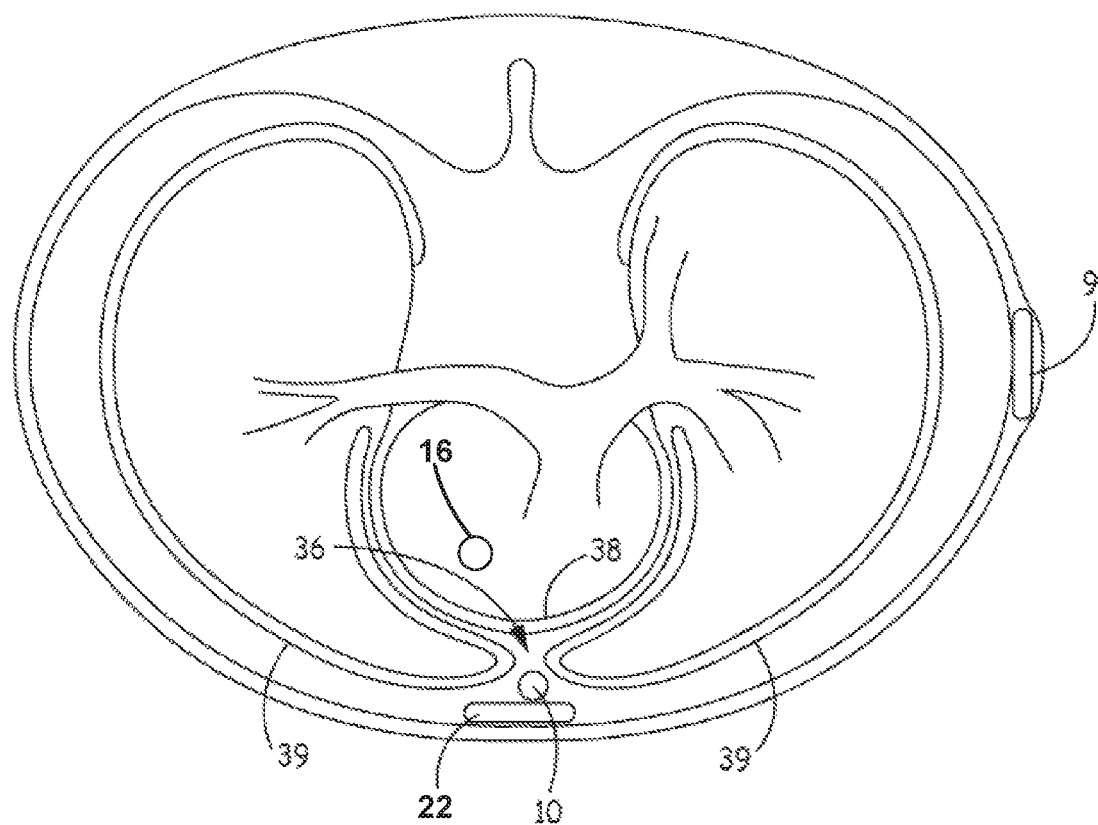
FIG. 2C is an example transverse view of a patient implanted with the example medical device system of FIG. 2A in accordance with one or more aspects of the present disclosure.

Defibrillation lead 25A may also include one or more sensing electrodes, such as sensing electrodes 32a and 32b, located along the distal portion of defibrillation lead 25A. In the example illustrated in FIG. 1, sensing electrodes 32a and 32b are separated from one another by defibrillation electrode 28. In other examples, however, sensing electrodes 32a and 32b may be both distal of defibrillation electrode 28 or both proximal of defibrillation electrode 28. In other examples, lead 25A may include more or fewer electrodes at various locations proximal and/or distal to defibrillation electrode 28, and lead 25A may include multiple defibrillation electrodes, e.g., such as defibrillation electrodes 28a and 28b as illustrated in FIGS. 2A-C. PD 16 may be configured to detect shocks delivered by ICD 9 via lead 25A.

Cardiac resynchronization therapy (CRT) is one type of therapy delivered by an IMD or group of IMDs such as ICD 9 and/or one or more PDs 16. CRT may help enhance cardiac output by resynchronizing the electromechanical activity of the ventricles of the heart. Ventricular dysynchrony may occur in patients that suffer from congestive heart failure (CHF). In CRT, the delivery of pacing pulses to the ventricle is timed to be a specified delay after the contraction of the atrium (A-V timing). In some examples, CRT involves delivery of pacing pulses to both ventricles ("biventricular pacing") to synchronize their contraction. In other examples, CRT involves delivery of pacing pulses to one ventricle to synchronize its contraction with that of the other ventricle, such as pacing the left ventricle to synchronize its contraction with that of the right ventricle.

One or more PDs 16 may provide pacing pulses to heart 26 based on the electrical signals sensed within heart 26 and/or in response to control signals transmitted to the PDs 16 from ICD 9. In some examples, PD 16 may provide pacing pulses in a manner that provides CRT to heart 26. In order to deliver CRT, it is necessary that the ventricular contraction occur at a specific time after the atrial contraction. In some cases, PD 16 cannot sense the atrial contraction and must receive from a separate device that can detect the atrial contraction a control signal that indicates when to deliver a pacing signal. In some examples, an PD 16 disposed in the left ventricle may be used in combination with another PD 16 disposed on the right ventricle to deliver biventricular pacing to the heart, which may provide CRT to the patient. In this manner, both PDs may receive the same or different control signals from ICD 9 according to the respective communication schedule. CRT may be used to treat heart failure-induced conduction disturbances and/or ventricular dyssynchrony. In some cases, CRT may help restore the mechanical sequence of ventricular activation and contraction. In some examples, CRT may involve biventricular pacing, e.g., via leads and/or PDs in the right and left ventricles, to synchronize the contraction of both ventricles. In other examples, CRT may involve pacing one of the ventricles, e.g., the left ventricle via PD 16, to synchronize its contraction with that of the other ventricle.

In one example, medical device system 8A includes an implantable medical device (e.g., PD 16) and another medical device (e.g., ICD 9) in communication with each other where ICD 9 operates as a master device transmitting control signals to PD 16 operating as a slave device receiving the control signals and performing the function commanded and/or triggered by the control signal. For example, ICD 9 may be configured to detect a cardiac event of patient 14, such as an atrial contraction (p-wave) and determine, based on the detected cardiac event, a timing for delivery of the therapy by PD 16 that is distinct from ICD 9. The therapy may be a pacing signal delivered by PD 16 to the left ventricle. ICD 9 may also determine a timing of a transmission window, the transmission window being one transmission window of a plurality of transmission windows defined by a transmission schedule and generate, based on the timing for delivery of the therapy and the timing of the transmission window, a control signal configured to define a time at which PD 16 is to deliver the therapy. ICD 9 may then transmit, during the transmission window defined by the transmission schedule, the control signal to PD 16. As discussed herein, ICD 9 may transmit information other than control signals (e.g., information indicative of a timing of the detected cardiac event) in other examples.

In concert with the transmission schedule of ICD 9, PD 16 may be independently enabling and disabling communication circuitry according to a communication schedule. PD 16 may initiate a communication window during which PD 16 is capable of receiving the control signal from ICD 9, the communication window being one communication window of a plurality of communication windows defined by a communication schedule that corresponds to the transmission schedule. PD 16 is generally not capable of receiving the control signal between the plurality of communication windows. After PD 16 receives, from ICD 9 and during the communication window, the control signal, PD 16 may then schedule delivery of the therapy at the time according to the control signal and deliver the therapy at the scheduled time. In this manner, PD 16 may be configured to deliver a pacing pulse to the left ventricle, for example, according to the commands provided by ICD 9 via the control signal, and may not be required to include sensing circuitry for sensing cardiac signals. However, in other examples, PD 16 may still be configured to sense cardiac events as a further check before delivering pacing pulses or to provide back-up pacing in the event that communication from ICD 9 has been lost. Although only one PD 16 is described, ICD 9 may use similar schedules to transmit information to one or more additional medical devices within patient 14. In addition, ICD 9 may include one or more intracardiac leads instead of, or in addition to, lead 25A. In other examples, PD 16 may communication with a master device in an atrium of heart 26, or in the right ventricle of heart 26, that may be a similar PD. The PD implanted in the right atrium or right ventricle may be the master device because it may be larger in size to accommodate a larger battery, sensing circuitry, or any other circuitry and/or functionality that may benefit a master device. The left ventricle implanted PD 16 may be constructed as a slave device to have limited functionality and a small size to comply with the size constraints of being implanted within the left ventricle. In another example, a subcutaneous monitor may detect cardiac events and transmit signals to PD 16.

FIG. 2A, FIG. 2B, and FIG. 2C are conceptual diagrams illustrating various views of another example cardiac medical device system 8B implanted within a patient 14. Components with like numbers in FIG. 1, FIG. 2A, FIG. 2B, and FIG. 2C may be similarly configured and may provide similar functionality. With reference to FIG. 2A, cardiac system 8B includes an extracardiovascular ICD system 30B implanted in patient 14 and a pacing device (PD) 16 implanted within heart 26 of patient 14. FIG. 2A is a front view of a patient implanted with the cardiac system 8B of FIG. 2A. FIG. 2B is a side view of the patient implanted with the cardiac system 8B of FIG. 2A. FIG. 2C is a transverse view of the patient implanted with the cardiac system 8B of FIG. 2A. Medical device system 8B as illustrated in FIG.

2A, FIG. 2B, and FIG. 2C may be configured to perform one or more of the techniques described herein with respect to medical device system 8A of FIG. 1. As described herein, medical device system 8 may refer to either 8A or 8B of FIGS. 1, 2A, 2B, and 2C, and ICD system 30 may refer to ICD system 30A or 30B of FIGS. 1, 2A, 2B, and 2C. With respect to FIGS. 1, 2A, 2B, and 2C, and elsewhere herein, PD 16 is generally described as being attached within a chamber of heart 26 (i.e., an intracardiac pacing device). However, in other examples, PD 16 may be attached to an external surface of heart 26 (e.g., in contact with the epicardium) such that PD 16 is disposed outside of heart 26, but is capable of pacing a desired chamber. Therefore, although PD 16 is generally described herein as a pacing device for intracardiac implantation, PD 16 may alternatively be configured to attach to an external surface of heart 26 and operate as an extracardiac pacing device.

Referring again to FIG. 2A, ICD system 30B includes an implantable cardioverter-defibrillator (ICD) 9 connected to at least one implantable cardiac defibrillation lead 25B. ICD 9 is configured to deliver high-energy cardioversion or defibrillation pulses to a patient's heart when atrial or ventricular fibrillation is detected. Cardioversion shocks are typically delivered in synchrony with a detected R-wave when fibrillation detection criteria are met. Defibrillation pulses are typically delivered when fibrillation criteria are met, and the R-wave cannot be discerned from signals sensed by ICD 9.

ICD 9 of FIG. 2A is implanted subcutaneously or submuscularly on the left side of patient 14 above the ribcage. Unlike defibrillation lead 25A of FIG. 1, defibrillation lead 25B of FIG. 2A may be implanted at least partially in a substernal location in FIG. 2A, e.g., between the ribcage and/or sternum 22 and heart. In one such configuration, a proximal portion of lead 25B extends subcutaneously from ICD 9 toward the sternum and a distal portion of lead 25B extends superior under or below the sternum 22 in the anterior mediastinum 36. The anterior mediastinum 36 is bounded laterally by the pleurae 39 (see FIG. 2C), posteriorly by the pericardium, and anteriorly by the sternum 22. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 25B extends along the posterior side of the sternum 22 substantially within the loose connective tissue and/or substernal musculature of the anterior mediastinum. Lead 25B may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 22 or ribcage.

In other examples, lead 25B may be implanted at other extracardiovascular locations. For example, defibrillation lead 25B may extend subcutaneously above the ribcage from ICD 9 toward a center of the torso of patient 14, bend or turn near the center of the torso, and extend subcutaneously superior above the ribcage and/or sternum 22, similar to that shown in FIG. 1. Defibrillation lead 25B may be offset laterally to the left or the right of the sternum 22 or located over the sternum 22. Defibrillation lead 25B may extend substantially parallel to the sternum 22 or be angled lateral from the sternum 22 at either the proximal or distal end. In another example, the defibrillation lead 25B and/or a pacing or sensing lead may be implanted within the pericardial sac, within the pericardium, epicardially, or at another location.

Defibrillation lead 25B of FIG. 2A includes an insulative lead body having a proximal end that includes a connector configured to be connected to ICD 9 and a distal portion that includes one or more electrodes. Defibrillation lead 25B also includes one or more conductors that form an electrically conductive path within the lead body and interconnect the electrical connector and respective ones of the electrodes.

Defibrillation lead 25B of FIG. 2A includes a defibrillation electrode that includes two sections or segments 28a and 28b, collectively (or alternatively) defibrillation electrodes 28. The defibrillation electrodes 28 of FIG. 2A are toward the distal portion of defibrillation lead 25B, e.g., toward the portion of defibrillation lead 25B extending along the sternum 22. Defibrillation lead 25B of FIG. 2A is placed below and/or along sternum 22 such that a therapy vector between defibrillation electrodes 28a or 28b and a housing electrode formed by or on ICD 9 (or other second electrode of the therapy vector) is substantially across a ventricle of heart 26. The therapy vector may, in one example, be viewed as a line that extends from a point on defibrillation electrodes 28 (e.g., a center of one of the defibrillation electrode sections 28a or 28b) to a point on the housing electrode of ICD 9. Defibrillation electrode 28 of FIG. 2A may, in one example, be an elongated coil electrode.

Defibrillation lead 25B may also include one or more sensing electrodes, such as sensing electrodes 32a and 32b, located along the distal portion of defibrillation lead 25B. In the example illustrated in FIG. 2A and FIG. 2B, sensing electrodes 32a and 32b are separated from one another by defibrillation electrode 28a. In other examples, however, sensing electrodes 32a and 32b may be both distal of defibrillation electrode 28 or both proximal of defibrillation electrode 28. In other examples, lead 25B may include more or fewer electrodes at various locations proximal and/or distal to defibrillation electrode 28. In the same or different examples, ICD 9 may include one or more electrodes on another lead (not shown).

ICD system 30B may sense electrical signals via one or more sensing vectors that include combinations of electrodes 32a and 32b and the housing electrode of ICD 9. For example, ICD 9 may obtain electrical signals sensed using a sensing vector between electrodes 32a and 32b, obtain electrical signals sensed using a sensing vector between electrode 32b and the conductive housing electrode of ICD 9, obtain electrical signals sensed using a sensing vector between electrode 32a and the conductive housing electrode of ICD 9, or a combination thereof. In some instances, ICD 9 may sense cardiac electrical signals using a sensing vector that includes one of the defibrillation electrode sections 28a and 28b (or electrode 28 in FIG. 1) and one of sensing electrodes 32a and 32b or the housing electrode of ICD 9.

The sensed electrical intrinsic signals may be indicative of one or more cardiac events and include electrical signals generated by cardiac muscle and indicative of depolarizations and repolarizations of heart 26 at various times during the cardiac cycle. Additionally, the sensed electrical signals may also include electrical signals, e.g., pacing pulses, generated and delivered to heart 26 by PD 16. ICD 9 analyzes the electrical signals sensed by the one or more sensing vectors to detect tachyarrhythmia, such as ventricular tachycardia or ventricular fibrillation. In response to detecting the tachyarrhythmia, ICD 9 may begin to charge a storage element, such as a bank of one or more capacitors, and, when charged, deliver one or more defibrillation pulses via defibrillation electrodes 28 (e.g., 28, 28a, 28b) of defibrillation lead 25B if the tachyarrhythmia is still present.

In the example of FIG. 2A, PD 16 is implanted within the left ventricle of heart 26 to provide pacing pulses for CRT therapy. PD 16 may be constructed of a size configured to fit within the available volume of the left ventricle and be attachable to a wall of the left ventricle. A smaller size of PD 16 may also reduce the risk of thrombus forming in the heart. PD 16 may leverage sensing capabilities of ICD 9 and therefore not include sensing circuitry and/or utilize a smaller capacity battery if regular sensing for cardiac events is not needed. For example, ICD 9 may be configured to sense electrical activity of heart 26, e.g., atrial depolarizations or P-waves, and determine when PD 16 should deliver one or more pacing signals (e.g., pulses) to the left ventricle. ICD 9 may then transmit control signals to PD 16, and PD 16 may receive the control signals and deliver pacing signals according to the timing indicated by the control signals. ICD 9 and PD 16 may operate using transmission schedules and communication schedules in order to limit the amount of time that PD 16 powers on communication circuitry that receives the control signals.

In some examples, ICD 9 may also provide pacing signals as part of the CRT therapy using electrodes 32a and/or 32b of lead 25B, for example. In other examples, ICD 9 may be coupled to one or more intracardiac leads carrying respective electrodes configured to be disposed within the right atrium and the right ventricle and deliver pacing pulses via these intracardiac leads as part of the CRT therapy along with PD 16. In other examples, additional PDs similar to PD 16 may be disposed within the right atrium and/or right ventricle. The PDs placed within the right atrium and/or right ventricle may be similarly controlled by ICD 9, or, one or both of the PDs in the right atrium and/or right ventricle may provide control signals to PD 16 in the left ventricle.

In other examples, PD 16 may be configured to deliver pacing therapy such as bradycardia pacing therapy and/or post-shock pacing, to heart 26. In these cases, PD 16 may be attached to an interior wall of the right ventricle of heart 26 via one or more fixation elements that penetrate the tissue. These fixation elements of PD 16 may secure PD 16 to the cardiac tissue and retain an electrode (e.g., a cathode or an anode) in contact with the cardiac tissue. However, in other examples, system 8B may include additional pacing devices 16 within respective chambers of heart 26 (e.g., right or left atrium and/or right ventricle).

In some examples, PD 16 may not include sensing circuitry. In other examples, PD 16 may be capable sensing electrical signals using the electrodes carried on the housing of PD 16. These electrical signals may be electrical signals generated by cardiac muscle and indicative of depolarizations and repolarizations of heart 26 at various times during the cardiac cycle. PD 16 may analyze the sensed electrical signals to detect tachyarrhythmias, such as ventricular tachycardia or ventricular fibrillation, bradyarrhythmias, or even shocks. In response to detecting these conditions, PD 16 may, e.g., depending on the type of arrhythmia or shock, begin to deliver bradycardia pacing therapy or post-shock pacing with or without information from another device. In some examples, PD 16 may only detect arrhythmias in response to failing to detect control signals from ICD 9 for a predetermined period of time or number of communication windows.

Although PD 16 and ICD 9 may be capable of at least one-way communication, cardiac PD 16 and ICD system 30B may be configured to operate completely independent of one another. In such a case, PD 16 and ICD system 30B are not capable of establishing telemetry or other communication sessions with one another to exchange information about sensing and/or therapy using one-way or two-way communication. This independent operation may be intentional or the result of a failure to synchronize transmission and communication schedules or some other error with one or both devices. Instead of sharing information, each of PD 16 and ICD system 30B analyze the data sensed via their respective electrodes to make arrhythmia detection and/or therapy decisions. As such, each device may not know if the other will detect the arrhythmia, if or when it will provide therapy, and the like.

Although FIG. 2A is shown or described in the context of a substernal ICD system 30 and a PD 16, techniques in accordance with one or more aspects of the present disclosure may be applicable to other coexistent systems. For example, an ICD system may include a lead having a distal portion that is implanted subcutaneously above the sternum (or other location) instead of being implanted substernally, in a manner similar to that shown in FIG. 1. In another example, instead of an ICD system, a pacing device coupled to two intracardiac leads may be implanted within the patient. In this manner, the pacing device may provide pacing pulses to the right atrium and ventricle via the intracardiac leads and control PD 16 to provide pacing pulses to the left ventricle. As such, the examples of FIG. 1, FIG. 2A, FIG. 2B, and FIG. 2C are illustrated for example purposes only and should not be considered limiting of the techniques described herein.

External device 21 may be configured to communicate with one or both ICD system 30A (FIG. 1) or ICD system 30B and PD 16 (FIG. 2A). External device 21 is described below with respect to ICD system 30B and PD 16 in FIG. 2A; however, external device 21 may operate similarly with respect to ICD system 30A of FIG. 1. In examples where external device 21 only communicates with one of ICD system 30B and PD 16, the non-communicative device may receive instructions from or transmit data to the device in communication with device 21. In some examples, device 21 comprises a handheld computing device, computer workstation, or networked computing device. Device 21 may include a user interface that is configured to receive input from a user. In other examples, the user may also interact with device 21 remotely via a networked computing device. The user may interact with device 21 to communicate with PD 16 and/or ICD system 30B. For example, the user may interact with device 21 to send an interrogation request and retrieve therapy delivery data, update therapy parameters that define therapy, manage communication between PD 16 and/or ICD system 30B, or perform any other activities with respect to PD 16 and/or ICD system 30B. Although the user is a physician, technician, surgeon, electrophysiologist, or other healthcare professional, the user may be patient 14 in some examples.

Device 21 may also allow the user to define how PD 16 and/or ICD system 30B senses electrical signals (e.g., ECGs), detects arrhythmias (e.g., tachyarrhythmias), delivers therapy, and communicates with other devices of system 8B. For example, device 21 may be used to change tachyarrhythmia detection parameters. In another example, device 21 may be used to manage therapy parameters that define therapies. In examples in which PD 16 and ICD system 30B communicate, device 21 may be used to alter communication protocols between PD 16 and ICD system 30B. For example, device 21 may instruct PD 16 and/or ICD system 30B to switch between one-way and two-way communication and/or change which of PD 16 and/or ICD system 30B are tasked with initial detection of arrhythmias. External device 21 may program A-V and/or V-V delays for CRT therapy. External device 21 may also, or alternatively, be configured to adjust parameters defining communication such as the duration of windows, the rate of windows, rate of synchronization signals, allowable lapses in communication before one or more devices attempt to re-establish communication, and other such parameters.

Device 21 may communicate with PD 16 and/or ICD system 30B via wireless communication using any techniques known in the art. Examples of communication techniques may include, for example, proprietary and non-proprietary radiofrequency (RF) telemetry, inductive telemetry, acoustics, and tissue conduction communication (TCC), but other techniques are also contemplated. During TCC, current is driven through the tissue between two or more electrodes of a transmitting device. The electrical signal spreads and can be detected at a distance by measuring the voltage generated between two electrodes of a receiving device. In some examples, device 21 may include a programming head that may be placed proximate to the patient's body near the PD 16 and/or ICD system 30B implant site in order to improve the quality or security of communication between PD 16 and/or ICD system 30B and device 21.

PD 16 may be configured to provide CRT or other pacing regimens or even adjust cardiac therapy based on the application of anti-tachyarrhythmia shock therapy by ICD 9. It may be useful that PD 16 knows when ICD 9 has delivered tachyarrhythmia shock therapy. In response to the delivery of the shock, PD 16 may activate post-shock pacing. In some examples, ICD 9 may transmit a control signal indicating that a shock is imminent or that PD 16 should begin pacing, e.g., at a time after the control signal indicated by the control signal.

In some examples, PD 16 and ICD system 30B may engage in communication to facilitate the appropriate detection of arrhythmias. The communication may include one-way communication in which one device is configured to transmit communication messages and the other device is configured to receive those messages according to the respective schedule. The communication may instead include two-way communication in which each device is configured to transmit and receive communication messages. Both of PD 16 and ICD 9 may be configured to toggle between one-way communication modes and two-way communication modes based on the therapy needed by the patient.

In combination with, or as an alternative to, communication between PD 16 and ICD system 30B, PD 16 may be configured to detect an anti-tachyarrhythmia shock delivered by ICD system 30B or an external defibrillator according to the detection of an electrical signal across two or more electrodes of PD 16. PD 16 may be configured to detect an anti-tachyarrhythmia shock based on electrical characteristics of the anti-tachyarrhythmia shock. Even though different defibrillation devices may provide different waveforms, including different pulse durations and amplitudes, defibrillation pulses generally have electrical signal characteristics such that detection of an anti-tachyarrhythmia shock can occur even without prior knowledge as to an anti-tachyarrhythmia shock waveform of an implanted or external defibrillator. In this manner, PD 16 may coordinate the delivery of cardiac stimulation therapy, including delivery of post-shock pacing.

In some examples, PD 16 detects the anti-tachyarrhythmia shock by measuring the voltage across the electrode inputs of the implanted device. PD 16 may detect one or more signal characteristics of an anti-tachyarrhythmia shock including: detection of the high amplitude level of an anti-tachyarrhythmia shock, detection of a high slew rate of the leading and trailing edges, and detection of a large post-shock polarization change. Detection of more than one signal characteristic may improve sensitivity and/or specificity. For example, PD 16 may detect a high level of an anti-tachyarrhythmia shock in combination with one or both of the detection of a high slew rate of the leading and trailing edges, and the detection of a large post-shock polarization change.

In response to detection of the anti-tachyarrhythmia shock, the PD 16 may activate post-shock pacing, such as VVI (Ventricular sensing, Ventricular pacing, Inhibited pacing when activity sensed) post-shock pacing. Post-shock pacing may be used to insure pacing support if the patient's heart does not begin to beat normally immediately following an anti-tachyarrhythmia shock. The pacing device may deliver post-shock pacing with a higher than normal pulse amplitude and pulse width (relative to typical cardiac pacing) to minimize the risk of loss of capture following an anti-tachyarrhythmia shock. A higher capture threshold may occur as a result of tissue stunning due to elevated current in the myocardial tissue from the anti-tachyarrhythmia shock delivery. A higher threshold may also occur as a result of physiological changes in the tissue resulting from lack of blood flow to the myocardium during ventricular fibrillation (VF). Furthermore, after an anti-tachyarrhythmia shock there can be increased polarization at the lead interface resulting in the need for a higher voltage to overcome the lead polarization.

In one example, PD 16 may deliver post-shock pacing to heart 26 via at least a subset of the set of electrodes of PD 16. In some examples, PD 16 may deliver the post-shock pacing after entering a post-shock pacing mode in response to detecting the shock. In some examples, PD 16 may use a timer to determine when a predetermined time has elapsed, during which the shock should have been delivered. PD 16 may begin post-shock pacing after the predetermined period has elapsed and/or stop post-shock pacing.

Although ICD 9 and PD 16 may perform coordinated communication in order to provide independent pacing or CRT, these medical devices may provide other therapies to patient 14 using transmission and communication schedules described herein. For example, ICD 9 may be a subcutaneous, substernal, or transvenous device that detects the atrial contraction (i.e., p-wave) and transmits the control signal telling a leadless pacer in the left ventricle (LV) (e.g., PD 16) when to deliver a pacing signal in order to add CRT to the functionality of the ICD 9. In another example, a small device may be implanted subcutaneously in the upper torso of patient 14 to detect the atrial contraction (p-wave) and transmit a control signal to PD 16 in the left ventricle, or PDs in both ventricles, in order to deliver CRT.

In other examples, the system may include a leadless dual chamber (e.g., DDD) pacemaker system including one PD 16 in the right atrium that senses the atrial contraction and transmits a control signal to a second PD 16 in the right ventricle in order to achieve atrioventricular (A-V) synchronous pacing. In some examples, the ventricular PD 16 may be configured to sense pre-ventricular contractions (PVCs) and transmit indications of the PVCs to the PD 16 in the atrium. In another example, two PD 16 devices may be in communication during ventricular pacing with atrial sensing (VDD) with one PD 16 in the right ventricle to detect P wave, deliver pacing signals to and sense activity from the right ventricle, and send a TCC signal to a PD 16 in the left ventricle to deliver a pacing signal to implement atrial synchronous bi-ventricular (bi-V) pacing. This pacing mode may avoid pacing on a T-wave following a PVC because the PD 16 in the right ventricle provides sensing and also provides backup ventricular pacing and sensing with ventricular event inhibition (VVI) pacing therapy if the TCC signals between the devices are lost.

Another therapy that may include communication is a device providing atrial pacing (AAI) in the right atrium to pace and sense in right atrium when needed, and sending a TCC signal to a PD 16 within the right ventricle to provide pacing to the right ventricle. The PD 16 in the right ventricle may be configured to sense cardiac activity in order to detect T-waves following PVCs and/or provide a backup VVI mode in the event that communication between the atrial and the ventricular devices is interrupted. In another example, a leaded device may provide DDD in the right atrium and the right ventricle to pace and sense in right atrium when needed, and send a TCC signal to an additional PD 16 in the left ventricle to implement three chamber pacing (e.g., right ventricular sensing may avoid right ventricular and/or left ventricular pacing on the T-wave after a PVC and provide a backup VVI mode). In another example, a leaded CRT device where the normal left ventricular lead is implanted in a location that does not result in adequate CRT response may benefit from incorporation of a left ventricular disposed PD 16. In this manner, the PD 16 may provide left ventricular pacing where the other lead in the left ventricle is disabled. In another example, PD 16 may deliver pacing to the LV in addition to pacing delivered via an LV lead to provide stimulation to two locations in the LV. This multi-point pacing may better synchronize the contraction throughout the LV than using only a single pacing point. In this example, the leaded CRT device sends a TCC signal to the PD 16 in the left ventricle to command pacing by the PD and thereby implement three chamber pacing and sensing. In some examples, a lead that is not used for pacing or sensing may be used to transmit a control signal or other signal from the leaded device to the PD 16. These and other examples of multiple medical device systems may incorporate the communication schemes described herein to reduce power consumption by limiting the amount of time the communication circuitry is powered in the receiving device.

Figure 3:
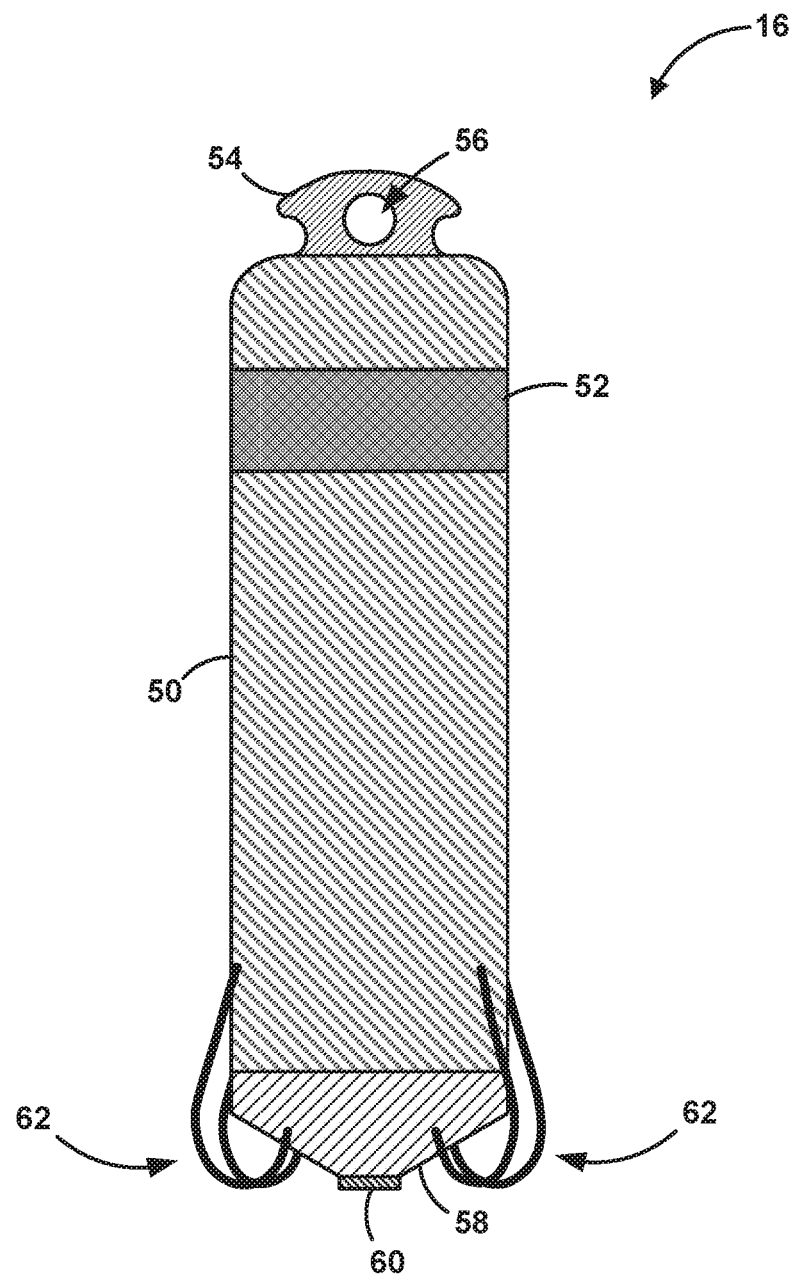
FIG. 3 is a conceptual drawing illustrating the example PD of FIG. 1 in accordance with one or more aspects of the present disclosure.

FIG. 3 is a conceptual drawing illustrating example PD 16 of FIG. 1 that may include communication circuitry and therapy circuitry configured to delivery pacing pulses and/or shocks to the patient. In some examples, PD 16 may include sensing circuitry as well. As shown in FIG. 3, PD 16 includes case 50, cap 58, electrode 60, electrode 52, fixation mechanisms 62, flange 54, and opening 56. Together, case 50 and cap 58 may be considered the housing of PD 16. In this manner, case 50 and cap 58 may enclose and protect the various electrical components within PD 16. Case 50 may enclose substantially all of the electrical components, and cap 58 may seal case 50 and create the hermetically sealed housing of PD 16. Although PD 16 is generally described as including one or more electrodes, PD 16 may typically include at least two electrodes (e.g., electrodes 52 and 60) to deliver an electrical signal (e.g., therapy such as a pacing signal or shock) and/or provide at least one sensing vector.

Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering pacing stimulation therapy such as, CRT or post-shock pacing. However, electrodes 52 and 60 may be used in any stimulation configuration. In addition, electrodes 52 and 60 may be used to detect intrinsic electrical signals from cardiac muscle. In other examples, PD 16 may include three or more electrodes, where each electrode may deliver therapy and/or detect intrinsic signals Electrodes 52 and 60, and any other electrodes carried by PD 16, may be configured to send and/or receive TCC signals in accordance with the disclosure herein.

Fixation mechanisms 62 may attach PD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of PD 16. For example, a suture or other device may be inserted around flange 54 and/or through opening 56 and attached to tissue. In this manner, flange 54 may provide a secondary attachment structure to tether or retain PD 16 within heart 26 if fixation mechanisms 62 fail. Flange 54 and/or opening 56 may also be used to extract PD 16 once the PD needs to be explanted (or removed) from patient 14 if such action is deemed necessary.

The techniques described herein are generally described with regard to a leadless pacing device or intracardiac pacing device such as PD 16. An intracardiac pacing device, such as PD 16, may be generally configured to be implanted within a chamber of the heart. In some examples, an intracardiac pacing device may be leadless, as shown in FIG. 3 with respect to PD 16. In other examples, an electrode, such as one or more of electrodes 52 and 60, may be carried on a small lead (e.g., a "leadlet") extending from case 50. However, even if the intracardiac pacing device includes one or more leadlets, the entire intracardiac pacing device, including the one or more leadlets, is still configured of a size that is implantable within a single chamber of the heart. PD 16 may be an example of an IMD configured to provide pacing in a chamber of a heart such as to support CRT therapy along with another IMD. However, alternative implantable medical devices may be used to perform the same or similar functions as PD 16, e.g., delivering cardiac pacing to heart 26 and communicating with ICD system 30 according to a communication schedule. For example, a PD may be configured to be implanted external to heart 26, e.g., near or attached to the epicardium of heart 26. An electrode carried by the housing of the PD may be placed in contact with the epicardium and/or one or more electrodes of leads coupled to the PD may be placed in contact with the epicardium at locations sufficient to provide therapy such as CRT or cardiac pacing generally (e.g., on external surfaces of the left and/or right ventricles). In some example, ICD system 30 may communicate with one or more leadless or leaded devices implanted internal or external to heart 26. For example, ICD system 30 may be configured to include sensing circuitry that detects cardiac events and transmit commands to an PD regarding what therapy should be delivered by the PD. In this manner, the PD may not include sensing circuitry and/or not be required to use battery power to sense cardiac events, which may result in a smaller PD that does not require sensing circuitry and/or larger battery capacity to operate the sensing circuitry.

Figure 4:
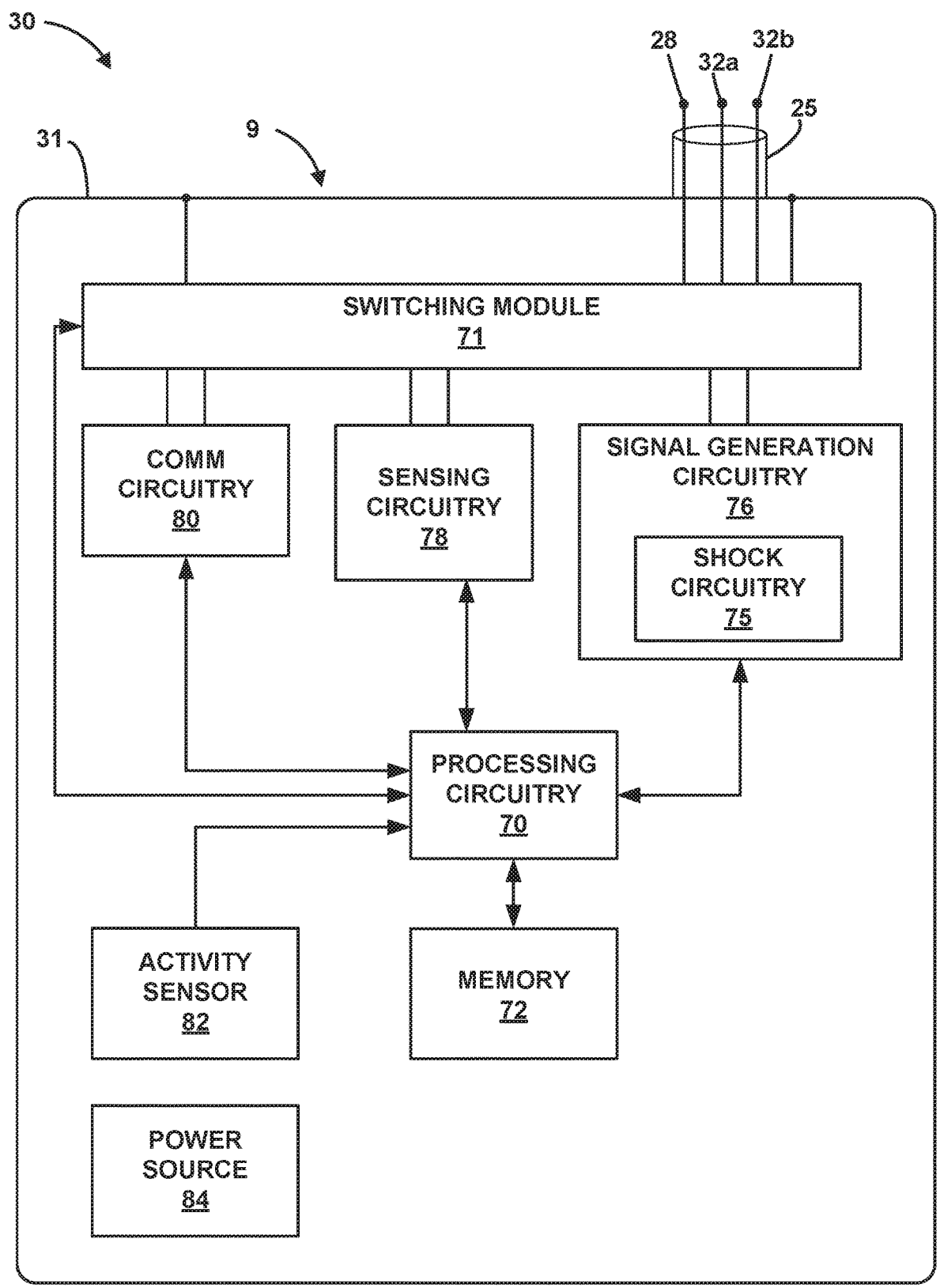
FIG. 4 is a functional block diagram illustrating an example configuration of the ICD of FIG. 1 in accordance with one or more aspects of the present disclosure.
Figure 5:
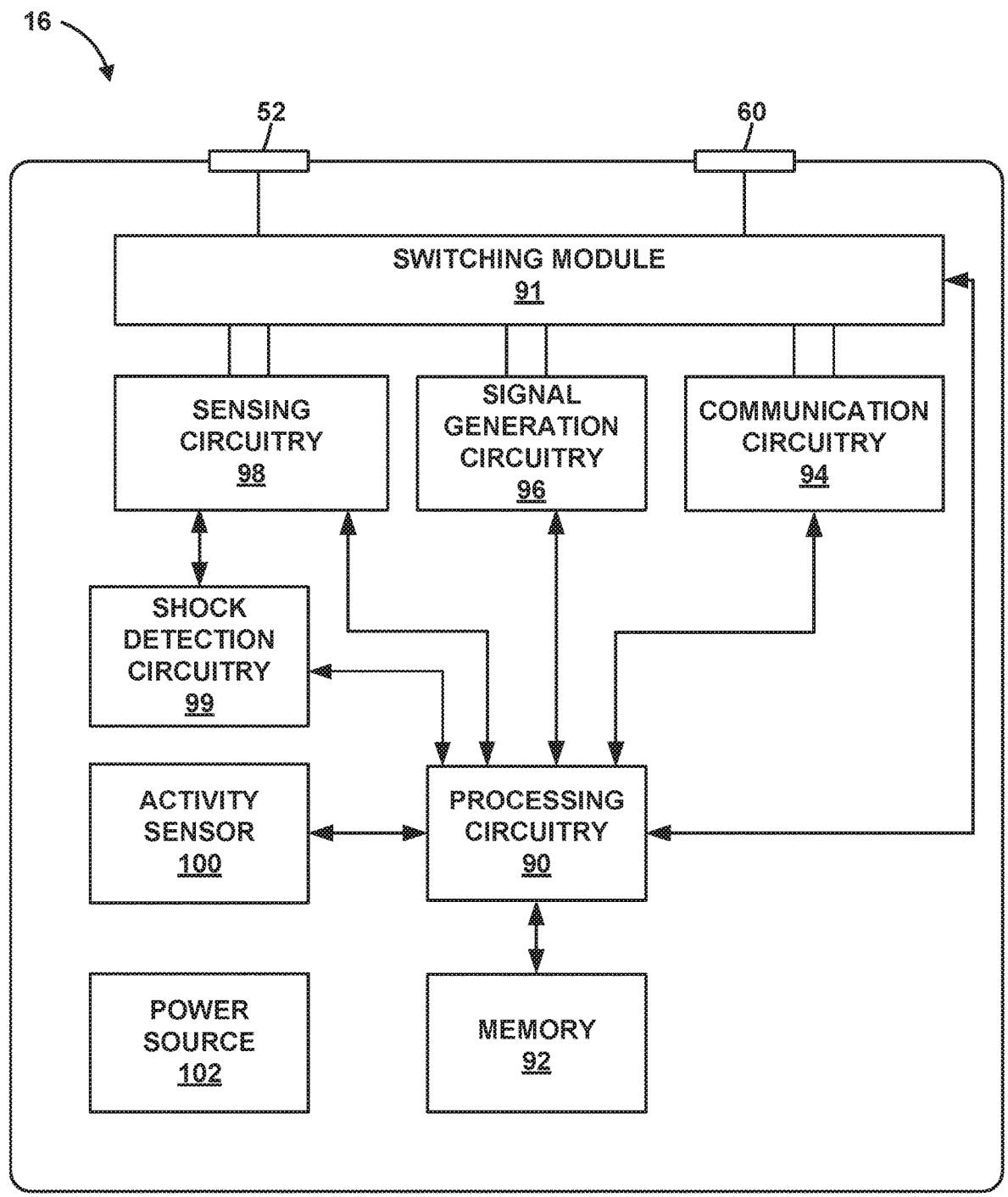
FIG. 5 is a functional block diagram illustrating an example configuration of the PD of FIG. 1 in accordance with one or more aspects of the present disclosure.

FIG. 4 is a functional block diagram illustrating an example configuration of ICD system 30 of FIG. 1. As described in connection with FIG. 1, ICD system 30 includes ICD 9 connected to at least one implantable cardiac defibrillation lead 25. As shown in FIG. 5, ICD system 30 includes a processing circuitry 70, switching module 71, memory 72, shock circuitry 75, signal generation circuitry 76, sensing circuitry 78, communication circuitry 80, activity sensor 82, and power source 84. Memory 72 includes computer-readable instructions that, when executed by processing circuitry 70, cause ICD system 30 and processing circuitry 70 to perform various functions attributed to ICD system 30 and processing circuitry 70 herein (e.g., detection of cardiac events such as p-waves, tachyarrhythmias, communication with PD 16, and/or delivery of anti-tachyarrhythmia shock therapy). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Communication circuitry 80, sensing circuitry 78, and signal generator 76 may be selectively coupled to electrodes 28 (or 28a or 28b), 32a, 32b, and the conductive housing electrode 31 of ICD 9 via switching module 71. Processing circuitry 70 may control switching module 71. Switching module 71 may be configured to selectively couple any of the electrodes to any of communication circuitry 80, sensing circuitry 78, and signal generator 76. The switching module may be configured to selectively couple the at least one electrode to sensing circuitry for sensing the physiological signal, therapy generation circuitry for delivering the therapeutic signals, or communication circuitry 80 for receiving and/or transmitting signals.

Processing circuitry 70 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 70 may include multiple components, such as any combination of one or more microprocessors, one or more controllers, one or more DSPs, one or more ASICs, or one or more FPGAs, as well as other discrete or integrated logic circuitry. The functions attributed to processing circuitry 70 herein may be embodied as software, firmware, hardware or any combination thereof.

Processing circuitry 70 controls signal generation circuitry 76 to deliver stimulation therapy to heart 26 according to therapy parameters, which may be stored in memory 72. For example, processing circuitry 70 may control signal generation circuitry 76 to deliver electrical pulses (e.g., shock pulses) with the amplitudes, pulse widths, frequency, or electrode polarities specified by the therapy parameters. In this manner, signal generation circuitry 76 may deliver electrical pulses to heart 26 via electrodes 28 (or 28a or 28b) and the conductive housing electrode 31 of ICD 9. In addition, any combination of electrodes, 28, 32a, 32b and/or housing 31 may be connected to sensing circuitry 78 via switching module 71. In further examples, signal generation circuitry 76 may deliver electrical pulses to heart 26, e.g., for cardiac pacing, via any combination of electrodes, 28, 32a, 32b and/or housing 31, although electrodes 32a and 32b may more frequently be used for sensing. ICD system 30 may use any combination of electrodes to deliver anti-tachycardia therapy and/or detect electrical signals from patient 14. However, in general, coil electrode 28 and housing 31 may be used to deliver an anti-tachyarrhythmia shock. If ICD 9 is provided with one or more cardiac leads, ICD 9 may also deliver pacing pulses to one or more chambers of the heart via the leads. In some examples, ICD 9 may deliver pacing pulses via an extravascular electrode, such as a can electrode and/or a substernal lead.

Signal generation circuitry 76 may also include shock circuitry 75. Shock circuitry 75 may include circuitry and/or capacitors required to deliver an anti-tachyarrhythmia shock. For example, signal generation circuitry 76 may charge shock circuitry 75 to prepare for delivering a shock. Shock circuitry 75 may then discharge to enable signal generation circuitry 76 to deliver the shock to patient 14 via one or more electrodes. In some examples, signal generation circuitry 76 and shock circuitry 75 may share one or more components, e.g., shock circuitry may be part of signal generation circuitry. In other examples, shock circuitry 75 may be located within ICD system 30 but separate from signal generation circuitry 76.

Signal generation circuitry 76 is electrically coupled to electrodes 28, 32a, and 32b via switching module 71. In the illustrated example, signal generation circuitry 76 is configured to generate and deliver electrical anti-tachyarrhythmia shock therapy to heart 26. For example, signal generation circuitry 76 may, using shock circuitry 75, deliver shocks to heart 26 via a subset of electrodes 28, 32a, and 32b. In some examples, signal generation circuitry 76 may deliver pacing stimulation (e.g., post-shock pacing), and cardioversion or defibrillation pulses in the form of voltage or current electrical pulses. In other examples, signal generation circuitry 76 may deliver one or more of these types of stimulation or shocks in voltage or current in the form of other signals, such as sine waves, square waves, or other substantially continuous time signals.

Signal generation circuitry 76 may include a switch module and processing circuitry 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing circuitry 78 may be configured to monitor signals from at least two of the electrodes 28, 32a, 32b and housing 31 in order to monitor cardiac events such as electrical activity of heart 26, impedance, or other electrical phenomenon, and/or other non-cardiac related activities. Sensing may be done to identify events within a cardiac cycle (e.g., p-waves, QRS complexes, t-waves, etc.) determine heart rates or heart rate variability, or to detect arrhythmias (e.g., tachyarrhythmia) or other electrical signals. Sensing circuitry 78 may utilize switching module 71 for selecting appropriate electrodes, but, alternatively, sensing circuitry 78 may include a separate or independent switch module to select which of the available electrodes are used to sense the heart activity, depending upon which electrode combination, or electrode vector, is used in the current sensing configuration. In examples with several electrodes, processing circuitry 70 may control switching module 71 to select the electrodes that function as sense electrodes, i.e., select the sensing configuration, via the switch module 71. Sensing module 78 may include one or more detection channels, each of which may be coupled to a selected electrode configuration for detection of cardiac signals via that electrode configuration. Some detection channels may be configured to detect specific cardiac events, such as P- or R-waves, and provide indications of the occurrences of such events to processing circuitry 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 70 may control the functionality of sensing module 78 by providing signals via a data/address bus.

Processing circuitry 70 may include a timing and control module, which may be embodied as hardware, firmware, software, or any combination thereof. The timing and control module may comprise a dedicated hardware circuit, such as an ASIC, separate from other processing circuitry 70 components, such as a microprocessor, or a software module executed by a component of processing circuitry 70, which may be a microprocessor or ASIC. The timing and control module may implement programmable counters. If ICD system 30 is configured to generate and deliver pacing pulses to heart 26, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processing circuitry 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing circuitry 78 for a time interval during and after delivery of electrical stimulation to heart 26. The durations of these intervals may be determined by processing circuitry 70 in response to stored data in memory 72. The timing and control module of processing circuitry 70 may also determine the amplitude of the cardiac pacing pulses. In addition, as described herein, processing circuitry 70 may determine the time for therapy delivery by another device, such as a pacing signal by PD 16, and generate a control signal for transmission to the PD 16 during a transmission window that indicates when the PD 16 is to deliver the pacing signal.

Interval counters implemented by the timing and control module of processing circuitry 70 may be reset upon sensing of R-waves and P-waves with detection channels of sensing circuitry 78. The value of the count present in the interval counters when reset by sensed R-waves and P-waves may be used by processing circuitry 70 to measure the durations of R-R intervals, P-P intervals, P-R intervals and R-P intervals, which are measurements that may be stored in memory 72. Processing circuitry 70 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 72 may be configured as a plurality of recirculating buffers, capable of holding series of measured intervals, which may be analyzed by processing circuitry 70 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processing circuitry 70 in other examples.

In some examples, processing circuitry 70 may determine that tachyarrhythmia has occurred by identification of shortened R-R (or P-P) interval lengths. Generally, processing circuitry 70 detects tachycardia when the interval length falls below 220 milliseconds and fibrillation when the interval length falls below 180 milliseconds. In other examples, processing circuitry 70 may detect ventricular tachycardia when the interval length falls between 330 milliseconds and ventricular fibrillation when the interval length falls between 240 milliseconds. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In the event that processing circuitry 70 detects an atrial or ventricular tachyarrhythmia based on signals from sensing circuitry 78, and an anti-tachyarrhythmia pacing regimen is desired, timing intervals for controlling the generation of anti-tachyarrhythmia pacing therapies by signal generation circuitry 76 may be loaded by processing circuitry 70 into the timing and control module to control the operation of the escape interval counters therein and to define refractory periods during which detection of R-waves and P-waves is ineffective to restart the escape interval counters for the an anti-tachyarrhythmia pacing. In addition to detecting and identifying specific types of cardiac rhythms, sensing circuitry 78 may also sample the detected intrinsic signals to generate an electrogram or other time-based indication of cardiac events.

Activity sensor 82 may be contained within the housing of ICD system 30 and include one or more accelerometers or other devices capable of detecting motion and/or position of ICD system 30. For example, activity sensor 82 may include a 3-axis accelerometer that is configured to detect accelerations in any direction in space. Accelerations detected by activity sensor 82 may be used by processing circuitry 70 to identify potential noise in signals detected by sensing circuitry 78 and/or confirm the detection of arrhythmias or other patient conditions. In some examples, activity sensor 82 may detect patient movement or movement of other organs such as breathing. In some examples, ICD 9 may include a microphone or other sensor configured to detect other physiological events such as heart sounds or breathing sounds. Processing circuitry 70 may analyze these physiological events in order to diagnose a condition of the patient and/or determine an appropriate therapy and/or timing of the therapy for the patient.

Power source 84 may be any type of device that is configured to hold a charge to operate the circuitry of ICD system 30. Power source 84 may be provided as a rechargeable or non-rechargeable battery. In other examples, power source 84 may also incorporate an energy scavenging system that stores electrical energy from movement of ICD system 30 within patient 14.

In some examples, communication circuitry 80 may be configured to detect communication signals from PD 16. PD 16 may generate electrical signals via one or more electrodes with amplitudes and/or patterns representative of information to be sent to ICD system 30. The electrical signals may be carried by pacing pulses or separate communication signals configured to be detected by ICD system 30. In this manner, communication circuitry 80 may be configured to monitor signals sensed by sensing circuitry 78 and determine when a communication message is received from PD 16. These signals sent via electrodes and through the patient may be referred to as tissue conduction communication (TCC).

As described herein, ICD system 30 may also transmit communication messages to PD 16 using electrical signals transmitted from one or more of electrodes 28, 32a, 32b and housing 31. In this case, communication circuitry 80 may generate and receive electrical signals or pulses via switching module 71 and one or more of electrodes. Processing circuitry 70 may control communication circuitry 80 and/or switching module 71 in order to transmit and/or receive communication signals. Alternatively, processing circuitry 70 may detect communications via sensing circuitry 78 and/or generate communications for deliver via signal generation circuitry 76. Although communication circuitry 80 may be used to communicate using electrical signals via electrodes 28, 32a, 32b and housing 31, communication circuitry 80 may alternatively or in addition use wireless protocols, such as RF telemetry, inductive telemetry, acoustics, or TCC to communicate with PD 16 or other medical devices. In some examples, communication circuitry 80 may include this wireless communication functionality.

Communication circuitry 80 includes any suitable hardware, firmware, software or any combination thereof for communicating with another device, such as PD 16 and/or device 21 (FIG. 1). Communication circuitry 80 may transmit generated or received arrhythmia data, therapy parameter values, communications between ICD system 30 and PD 16, control signals as commands for another medical device, or any other information. For example, communication circuitry 80 may transmit information representative of sensed physiological data such as R-R intervals or any other data that may be used by PD 16 to determine a condition of patient 14. Communication circuitry 80 may also be used to receive updated therapy parameters from device 21. Under the control of processing circuitry 70, communication circuitry 80 may receive downlink telemetry from and send uplink telemetry to device 21 with the aid of an antenna, which may be internal and/or external. Processing circuitry 70 may provide the data to be uplinked to device 21 and the control signals for the telemetry circuit within communication circuitry 80, e.g., via an address/data bus. In some examples, communication circuitry 80 may provide received data to processing circuitry 70 via a multiplexer.

Memory 72 may be configured to store a variety of operational parameters, therapy parameters, sensed and detected data, and any other information related to the monitoring, therapy and treatment of patient 14. Memory 72 may store, for example, A-V and/or V-V intervals, thresholds and parameters indicative of tachyarrhythmias and/or therapy parameter values that at least partially define delivered anti-tachyarrhythmia shocks. In some examples, memory 72 may also store communications transmitted to and/or received from PD 16. In addition, memory 72 may store information related to the communication regime employed between ICD 9 and other medical devices, such as transmission window durations, frequencies, control signal attributes, communication re-establishment protocols, synchronization times, and other such parameters defining communication.

In some examples, ICD system 30 may signal device 21 to further communicate with and pass the alert through a network such as the Medtronic CareLink® Network developed by Medtronic, Inc., of Minneapolis, MN, or some other network linking patient 14 to a clinician. ICD system 30 may spontaneously transmit the diagnostic information to the network or in response to an interrogation request from a user.

As described herein ICD system 30, including ICD 9, may be configured to communicate with other medical devices, such as PD 16 using a communication regime that limits the amount of time the receiver medical device needs to be listening for transmitted signals. In TCC, for example, the receiving medical device may need to power an amplifier of the communication circuitry in order to detect transmitted signals, and that amplification requires battery power. ICD system 30 may thus utilize a transmission schedule that is aligned in time, or synchronized, with a communication schedule of the receiving device in order to send signals to the receiving device. Although ICD system 30 is described herein as the transmitting medical device, or the master device, ICD system 30 may operate as a receiving device in some examples as well.

In one example, ICD system 30 operates as a master device transmitting control signals to PD 16 operating as a slave device receiving the control signals and performing the function commanded by the control signal. For example, ICD system 30 may be configured to detect a cardiac event of patient 14, such as an atrial contraction (p-wave) and determine, based on the detected cardiac event, a timing for delivery of the therapy by PD 16 (the PD 16 being separate and distinct from ICD system 30). The therapy may be a pacing signal delivered by PD 16 to the left ventricle. ICD system 30 may also determine a timing of a transmission window, the transmission window being one transmission window of a plurality of transmission windows defined by a transmission schedule and generate, based on the timing for delivery of the therapy and the timing of the transmission window, a control signal configured to define a time at which PD 16 is to deliver the therapy. ICD system 30 may then transmit, during the transmission window defined by the transmission schedule, the control signal to PD 16.

The control signal transmitted by ICD system 30 may indicate a delay period between the timing of the transmission window (i.e., the time that the control signal was transmitted) and the time at which the implantable medical device is to deliver the therapy. Therefore, when the receiving device receives the control signal, the receiving device can schedule therapy delivery for the appropriate time with respect to the received control signal. This delay period may allow control signals to be sent at times other than when the therapy is to be delivered, which can occur when transmission windows only occur at a certain rates, such as a rate between 10 Hz and 50 Hz, for example.

ICD system 30 may transmit multiple control signals indicative of the same therapy to be delivered by the receiving medical device (e.g., PD 16). Subsequent to detecting a cardiac event and determining the timing for when the appropriate therapy is to be delivered, as discussed above, ICD system 30 may determine a timing of a second transmission window subsequent to the first transmission window in which the first control signal was transmitted, the second transmission window being another transmission window of the plurality of transmission windows. ICD system 30 may then generate, based on the timing of the second transmission window and the timing for delivery of the therapy, a second control signal configured to define the time at which PD 16 is to deliver the therapy. The second control signal is indicative of a second delay period between the timing of the second transmission window and the time at which PD 16 is to deliver the pacing signal. ICD system 30 may then transmit the second control signal to PD 16 during the respective transmission window defined by the transmission schedule.

In this manner, multiple control signals may be transmitted during respective (and possibly consecutive) transmission windows. Each control signal may specify the same time for the therapy delivery by varying the delay period from the time each control signal is transmitted. For example, the first control signal may indicate that therapy is to be delivered in 90 ms and the second control signal, transmitted at a transmission window 50 ms later, may indicate that the therapy is to be delivered in 40 ms after the transmission of the second control signal. By transmitting multiple control signals for the same upcoming therapy event, the receiving device (e.g., PD 16) has an increased chance of detecting at least one of the signals and delivering the therapy at the appropriate time. In other words, even if PD 16 does not receive one of the control signals, PD 16 may detect the other control signal and responsively deliver the therapy at the appropriate time. The transmission and communication schedules of ICD system 30 and PD 16, for example, may be defined with sufficient rate of windows such that multiple windows will likely occur between the transmitting device detecting the cardiac event and the therapy needs to be delivered. However, only one window between cardiac event and therapy can provide sufficient communication between the devices, in which case ICD system 30 only sends one communication that includes the time to deliver therapy. In other examples, ICD system 30 may continue to transmit control signals indicating ever decreasing delay periods as long as transmission windows occur prior to the commanded therapy delivery.

The transmission schedule corresponds to a communication schedule of an implantable medical device on the receiving end (e.g., PD 16), wherein each communication window of the communication schedule is configured to align in time with respective transmission windows of the plurality of transmission windows. In this manner, the receiving implantable medical device is configured to enable communication circuitry to receive signals from ICD system 30 during each communication window and disable communication circuitry between each communication window of the communication schedule. The transmission window may be a period of time having some duration during which the transmission of the control signal can occur. However, the transmission window may be more of a point in time in other examples, where any transmission is scheduled to be delivered precisely at the time of the transmission window or at least the initiation of the transmission window. Each transmission window of the plurality of transmission windows may occur at a predetermined frequency or rate where each of the transmission windows are separated by a predetermined interval. For example, the predetermined rate may by approximately 10 Hz to approximately 50 Hz (with corresponding intervals of 100 milliseconds (ms) to 20 ms. In one example, the predetermined rate is from approximately 20 Hz to approximately 30 Hz (with corresponding intervals from approximately 50 ms to approximately 33 ms). The predetermined interval may correspond to similar frequencies but be expressed as intervals of a certain number of milliseconds, such as between approximately 20 ms and 100 ms. The interval may be the interval defined between the beginning of each transmission window or the rate of the transmission window, and not necessarily the interval between the end of one transmission window and the beginning of the next transmission window. However, the interval between windows may be used instead, and the inter-window intervals may take into account the duration of each window in order to achieve a desired rate for the transmission windows.

ICD system 30 may also incorporate blanking windows into the transmission schedule to refrain from sending signals during the blanking windows. For example, ICD system 30 may, responsive to transmitting a control signal, determining that a time period to the time at which the implantable medical device is to deliver the therapy is less than an interval to a next transmission window of the plurality of transmission windows that immediately follows the transmission window during which the control signal was transmitted. In other words, the next transmission window will not occur prior to the time of delivering the therapy. Responsive to determining that the time period is less than the interval, ICD system 30 may initiate a blanking window during which the first medical device is configured to refrain from transmitting signals to the implantable medical device during the blanking window. In some examples, ICD system 30 may stop powering the communication circuitry during this blanking window in order to conserve power for ICD system 30.

ICD system 30 may also transmit synchronization signals to the receiving medical device in order to maintain synchronicity between the transmission schedule and the communication schedule of ICD system 30 and PD 16, respectively. Since each medical device independently tracks timing of the respective transmission windows and communication windows, the clock signal used for this timing may vary between the devices. For example, PD 16 may include a less accurate clock than ICD system 30 to conserve power and/or reduce cost and/or reduce size of PD 16 relative to ICD 9. The synchronization signal sent from ICD system 30 may assist PD 16 in maintaining a communication schedule that is aligned with the transmission schedule even if the clocks of each device vary. For example, ICD system 30 may determine that the blanking window has elapsed and, responsive to determining that the blanking window has elapsed, transmit a synchronization signal to PD 16 during a next transmission window of the transmission schedule that immediately followed the blanking window. The synchronization signal transmitted by the ICD system 30 may control the implantable medical device (e.g., PD 16) to restart the communication schedule maintained by the implantable medical device. For example, PD 16 may move the communication schedule forward or backward in time based on whether the synchronization signal was detected earlier or later in time than expected. Although the synchronization signal may be sent once per cardiac cycle (e.g., after a blanking window), the synchronization signal may be sent more frequently or less frequently in other examples. PD 16 may synchronize the communication window to the transmission window based on when a control signal is received.

In some examples, ICD system 30 may monitor the operation of PD 16 as a check to ensure that PD 16 is receiving transmitted control signals. For example, ICD system 30 may control sensing circuitry 78 to sense for signals indicating that therapy was delivered by PD 16 (e.g., sense for a paced signal or any other therapy commanded by ICD system 30). Based on the sensed signals anticipated from, or resulting from, PD 16, ICD may take appropriate corrective action. In particular, not detecting signals associated with PD 16 activity may indicate that PD 16 is not receiving the control signals sent from ICD system 30. ICD system 30 may determine that PD 16 has not delivered a predetermined number of therapies (e.g., one, two, three, or more) expected by ICD system 30 based on the transmitted control signals. Responsive to determining that PD 16 has not delivered the predetermined number of therapies, ICD system 30 may increase the rate of the transmission windows of the transmission schedule. This increase in rate may increase the likelihood that ICD system 30 transmits a control signal during a communication window of the PD 16. ICD system 30 may iteratively increase the rate of transmission windows as the number of missed therapies are identified. Alternatively, or additionally, ICD system 30 may transmit a signal that triggers PD 16 to change from a therapy mode (e.g., a pacing mode) to a start-up or search mode in which ICD system 30 and PD 16 can re-synchronize the transmission and communication windows.

In this manner, ICD system 30 may change the transmission schedule as needed. In some examples, the transmission schedule, and communication schedule, may be altered based on physiological activity of the patient. These changes may be done to reduce communication activity between the devices while maintaining effective communication. For example, ICD system 30 may change the rate of the transmission schedule based on the A-V interval or heart rate. For example, longer A-V interval may support less frequent transmission windows while maintaining appropriate delay between one or more transmission windows and the timing of the therapy to be delivered. If ICD system 30 changes the transmission window, PD 16, or the receiving device, may detect the altered transmission schedule and make a corresponding adjustment to the communication window and/or communication schedule in order to maintain synchronization. Alternatively, ICD system 30 may send a request to PD 16 to enter a start-up mode or sync mode in order to re-establish the schedules with additional one-way or two-way communication with PD 16.

In one example, ICD system 30 (and PD 16) may increase or decrease the blanking window between the delivered therapy, e.g., a pacing pulse delivered by PD 16, and the synchronization signal. For example, for lower heart rates, the blanking window may be lengthened. If a standard blanking window is 400 ms, ICD system 30 may increase the blanking window to 500 ms or even 600 ms, for example, in order to further reduce the number of transmission windows and communication windows during which communication circuitry is drawing from each device. In other examples, ICD system 30 may determine the blanking window in order to maintain a predetermined number of transmission windows (e.g., three transmission windows) prior to the detection of the cardiac event. ICD system 30 may monitor the number of transmission windows in previous cardiac cycles and adjust the blanking window if fewer or greater transmission windows occur between the transmission window and the subsequent detected cardiac event. For example, if ICD system 30 determines that two cardiac cycles in a row occur with only two transmission windows before the cardiac event, but three transmission windows is the target number of transmission windows, ICD system 30 may reduce the duration of the subsequent blanking window by the duration of one interval between transmission windows. Therefore, ICD system 30 may increase or decrease the duration of the next blanking window to balance the length of the blanking window with a predetermined number of transmission windows desired prior to the next detected cardiac event. Similarly, PD 16 may be configured to adjust the length of the blanking window based on the number of transmission windows counted prior to receiving the first pace control signal. For example, PD 16 may lengthen the blanking window if more transmission windows than expected occur prior to the pacing control signal or shorten the banking window is fewer transmission windows occur prior to the pacing control signal being received from ICD system 30.

ICD system 30 may instruct PD 16 of the change in the blanking window with an explicit command, or PD 16 may infer that the blanking window has lengthened when one or more communication windows following the blanking window of PD 16 elapse without detecting a synchronization signal. In other words, PD 16 may operate with instructions that the synchronization signal is transmitted on the first transmission window following the blanking window. If ICD system 30 needs to reduce the blanking window, ICD system 30 may send a synchronization signal having information or a code that indicates that PD 16 should reduce the blanking window a certain amount of time for the next cardiac cycle.

As described herein, a master device that transmits information (e.g., ICD system 30) and a slave device that receives information (e.g., PD 16) may operate in different modes. A "therapy mode" may be the mode that ICD system 30 and PD 16 operate in most of the time to provide therapy. In the therapy mode, the master device sends one-way communication to the slave device as needed for therapy, such as every cardiac cycle if the slave device is providing pacing pulses. This therapy mode utilizing the transmission schedule and communication schedule described herein may allow for ultralow power consumption communication, particularly for the slave device that may have more restrictive power capacity limits (e.g., smaller devices with smaller batteries). The medical devices may also operate in other modes such as a "start-up" or "search" mode and a "programming" mode. These start-up and programming modes may require additional power, but these modes may only be needed infrequently.

During a start-up or search mode, the slave device is synchronized to the master device that transmits the information. The start-up mode may be performed after initial implantation, after a programming session for the master device, or if the slave device loses synchronization. During the start-up or search mode, the master device may provide more frequent and/or stronger signals than during the therapy mode, and the slave device may power up the communication circuitry more frequently, or even continuously, in order to detect the data transmitted by the master device. In some examples, the slave device may be configured to independently detect cardiac events to independently pace the chamber (e.g., a ventricle) until communication is re-established with the master device. Although this sensing may draw more power, it may be advantageous that the patient continues to receive therapy during this relatively short period of time.

During the programming mode, the master device may communicate extensively with the slave device, either in one-way communication or two-way communication. For example, the programming mode may include a threshold search by the slave device, and/or interrogating the slave device on battery status, electrode capture, therapy circuit impedance, or TCC signal strength. In this manner, the slave device may provide data back to the master device when answering these interrogations. The programming mode may be used infrequently, such as once per day or even less frequently. The programming mode may be scheduled or performed on demand by the master device, the slave device, or at the request of an external device such as external device 21 (FIG. 1). In some examples, changing of therapy parameters, transmission schedules and/or communication schedules, or any other operation changes may occur during the programming mode.

FIG. 5 is a functional block diagram illustrating an example configuration of PD 16 of FIG. 1. In the illustrated example, PD 16 includes a processing circuitry 90, memory 92, signal generation circuitry 96, sensing circuitry 98, shock detection circuitry 99, activity sensor 100, communication circuitry 94, and power source 102. In some examples, PD 16 may include more or fewer than these components. Memory 92 includes computer-readable instructions that, when executed by processing circuitry 90, cause PD 16 and processing circuitry 90 to perform various functions attributed to PD 16 and processing circuitry 90 herein (e.g., detecting arrhythmias, communicating with ICD system 30, and delivering therapies such as anti-tachycardia pacing and post-shock pacing as well as conventional brady pacing therapy). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Communication circuitry 94, sensing circuitry 98, and signal generation circuitry 96 may be selectively coupled to electrodes 52 and 60 via switching module 91. Processing circuitry 90 may control switching module 91. Switching module 91 may be configured to selectively couple any of the electrodes to any of communication circuitry 94, sensing circuitry 98, and signal generator 96. The switching module may be configured to selectively couple the at least one electrode to sensing circuitry for sensing the physiological signal, therapy generation circuitry for delivering the therapeutic signals, or communication circuitry 80 for receiving and/or transmitting signals.

Processing circuitry 90 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 90 may include multiple components, such as any combination of one or more microprocessors, one or more controllers, one or more DSPs, one or more ASICs, or one or more FPGAs, as well as other discrete or integrated logic circuitry. The functions attributed to processing circuitry 90 herein may be embodied as software, firmware, hardware or any combination thereof.

Processing circuitry 90 controls signal generation circuitry 96 to deliver stimulation therapy to heart 26 according to therapy parameters, which may be stored in memory 92. For example, processing circuitry 90 may control signal generation circuitry 96 to deliver electrical pulses with the amplitudes, pulse widths, frequency, or electrode polarities specified by the therapy parameters. In this manner, signal generation circuitry 96 may deliver pacing pulses (e.g., post-shock pacing therapy, CRT pacing pulses, or conventional bradycardia pacing pulses) to heart 26 via electrodes 52 and 60 and switching module 91. Although PD 16 may only include two electrodes, e.g., electrodes 52 and 60, PD 16 may utilize three or more electrodes in other examples. PD 16 may use any combination of electrodes to deliver therapy and/or detect electrical signals from patient 14.

Signal generation circuitry 96 is electrically coupled to electrodes 52 and 60 carried on the housing of PD 16 and via switching module 91. In the illustrated example, signal generation circuitry 96 is configured to generate and deliver electrical stimulation therapy to heart 26. For example, signal generation circuitry 96 may deliver the electrical stimulation therapy to a portion of cardiac muscle within heart 26 via electrodes 52 and 60. In some examples, signal generation circuitry 96 may deliver pacing stimulation, e.g., CRT therapy or post-shock pacing, in the form of voltage or current electrical pulses. In other examples, signal generation circuitry 96 may deliver one or more of these types of stimulation in the form of other signals, such as sine waves, square waves, or other substantially continuous time signals. Although PD 16 is generally described as delivering pacing pulses, PD 16 may deliver cardioversion or defibrillation pulses in other examples.

Therapy signals delivered from PD 16 may provide, at least partially, CRT therapy, bradycardia therapy, or therapies for other such disorders. Each of these signals may be defined by a set of parameters stored in memory 92, and may include parameters such as pulse intervals, pulse width, current and/or voltage amplitudes, and durations for each pacing mode. These parameters may include pulse intervals, pulse width, current and/or voltage amplitudes, and durations for each pacing mode. PD 16 may store these parameter values for therapy signals, although the pacing therapy commands received by PD 16 may encode various parameter values in some examples.

Parameters that define post-shock pacing may vary. In one example, monophasic post-shock pacing therapy may have a pulse width of approximately 1 millisecond at each phase and a pulse amplitude of approximately 5 volts. The pacing rate may be set to 30-60 beats per minute (0.5-1 hertz). The duration of each post-shock pacing session may be between 10 seconds and 60 seconds, or even longer in other examples. In other examples, pulse widths, pulse amplitudes, and/or durations of post-shock pacing may be greater or lower.

Electrical sensing circuitry 98 monitors signals from electrodes 52 and 60 in order to monitor electrical activity of heart 26, impedance, or other electrical phenomenon. Sensing may be done to determine heart rates or heart rate variability, or to detect arrhythmias (e.g., tachyarrhythmias or bradycardia) or other electrical signals. Sensing circuitry 98 may also include a switch module to select which of the available electrodes (or electrode polarity) are used to sense the heart activity, depending upon which electrode combination, or electrode vector, is used in the current sensing configuration. In examples with several electrodes, processing circuitry 90 may select the electrodes that function as sense electrodes, i.e., select the sensing configuration, via the switch module within sensing circuitry 98. Sensing circuitry 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processing circuitry 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 90 may control the functionality of sensing circuitry 98 by providing signals via a data/address bus. In some examples, PD 16 may not utilize electrical sensing circuitry 98 during therapy (e.g., when providing pacing based on commands from a master device).

Processing circuitry 90 may include a timing and control module, which may be embodied as hardware, firmware, software, or any combination thereof. The timing and control module may comprise a dedicated hardware circuit, such as an ASIC, separate from other processing circuitry 90 components, such as a microprocessor, or a software module executed by a component of processing circuitry 90, which may be a microprocessor or ASIC. The timing and control module may implement programmable counters. If PD 16 is configured to generate and deliver pacing pulses to heart 26, such counters may control the basic time intervals associated with DDD, VVI, DVI, VDD, AAI, DDI, DDDR, VVIR, DVIR, VDDR, AAIR, DDIR and other modes of pacing. Example PDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent Ser. No. 13/665,601 to Bonner et al. are both incorporated herein by reference in their entireties.

Intervals defined by the timing and control module within processing circuitry 90 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing circuitry 98 for a time interval during and after delivery of electrical stimulation to heart 26. The durations of these intervals may be determined by processing circuitry 90 in response to stored data in memory 92. The timing and control module of processing circuitry 90 may also determine the amplitude of the cardiac pacing pulses. In other examples, the intervals may be dictated by the control signals received from the master device, such as ICD system 30.

Interval counters implemented by the timing and control module of processing circuitry 90 may be reset upon sensing of R-waves and P-waves with detection channels of sensing circuitry 98. In examples in which PD 16 provides pacing, signal generation circuitry 96 may include pacer output circuits that are coupled to electrodes 52 and 60 via switching module 91, for example, appropriate for delivery of a bipolar or unipolar pacing pulse to one of the chambers of heart 26. In such examples, processing circuitry 90 may reset the interval counters upon the generation of pacing pulses by signal generation circuitry 96, and thereby control the basic timing of cardiac pacing functions, including post-shock pacing if such functionality is provided. However, as described herein, PD 16 may not include sensing circuitry 98 in other examples.

The value of the count present in the interval counters when reset by sensed R-waves and P-waves may be used by processing circuitry 90 to measure the durations of R-R intervals, P-P intervals, P-R intervals and R-P intervals, which are measurements that may be stored in memory 92. Processing circuitry 90 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 92 may be configured as a plurality of recirculating buffers, capable of holding series of measured intervals, which may be analyzed by processing circuitry 90 in response to the occurrence of a pace or sense interrupt to determine whether the patient's heart 26 is presently exhibiting atrial or ventricular tachyarrhythmia.

In addition to detecting and identifying specific types of cardiac rhythms, sensing circuitry 98 may also sample the detected intrinsic signals to generate an electrogram or other time-based indication of cardiac events. Processing circuitry 90 may also be able to coordinate the delivery of pacing pulses from different PDs implanted in different chambers of heart 26, such as an PD implanted in atrium and/or an PD implanted in left ventricle. For example, processing circuitry 90 may identify delivered pulses from other PDs via sensing circuitry 98 and update pulse timing to accomplish a selected pacing regimen. This detection may be on a pulse-to-pulse or beat-to-beat basis, or on a less frequent basis to make slight modifications to pulse rate over time. In other examples, PDs may communicate with each other via communication circuitry 94 and/or instructions over a carrier wave (such as a stimulation waveform). In this manner, pacing therapy may be coordinated from multiple PDs.

Shock detection circuitry 99 may be used to detect anti-tachyarrhythmia shocks delivered by ICD system 30 or another device. For example, processing circuitry 90 may enable shock detection circuitry 99 in response to detecting a tachyarrhythmia or receiving a communication indicating that an arrhythmia has been detected or a shock is imminent. Processing circuitry 90 may also disable shock detection circuitry 99 after a predetermined time period has elapsed or when a shock is otherwise not (or no longer) anticipated. When shock detection circuitry 99 is enabled, shock detection circuitry 99 may identify when an electrical signal received by sensing circuitry 98 is representative of a cardioversion or defibrillation pulse.

Although illustrated separately in the example of FIG. 5, shock detection circuitry 99 may, in some examples, be included as part of processing circuitry 90. In some examples, the shock detection functionality attributed to shock detection circuitry 99 may be a functional module executed by processing circuitry 90. Similar to shock detection, other sensing functionality may include specific circuitry for detecting a certain cardiac event or other signals. For example, circuitry for detecting ventricular contractions may be provided as part of, or separate from, sensing circuitry 98. In other examples, communication circuitry 94 may be directly coupled to sensing circuitry 98 in order to detect transmitted signals via TCC as described herein.

Memory 92 may be configured to store a variety of operational parameters, therapy parameters, sensed and detected data, communication instructions, and any other information related to the therapy and treatment of patient 14. In the example of FIG. 5, memory 92 may store sensed ECGs, detected arrhythmias, communications from ICD system 30, and therapy parameters that define pacing regimens. In other examples, memory 92 may act as a temporary buffer for storing data until it can be uploaded to ICD system 30, another implanted device, or device 21. Memory 92 may also store parameters defining the communication regime such as communication schedules and communication windows, translations for codes provided by different control signals and/or synchronization signals, communication error handing instructions, and the like.

Activity sensor 100 may be contained within the housing of PD 16 and include one or more accelerometers or other devices capable of detecting motion and/or position of PD 16. For example, activity sensor 100 may include a 3-axis accelerometer that is configured to detect accelerations in any direction in space. Specifically, the 3-axis accelerator may be used to detect PD 16 motion that may be indicative of cardiac events and/or noise. For example, processing circuitry 90 may monitor the accelerations from activity sensor 100 to confirm or detect arrhythmias. Since PD 16 may move with a chamber wall of heart 26, the detected changes in acceleration may also be indicative of contractions. Therefore, PD 16 may be configured to identify heart rates and confirm arrhythmias, such as a tachycardia, sensed via sensing circuitry 98.

In some examples, PD 16 may signal device 21 to further communicate with and pass the alert through a network such as the Medtronic CareLink® Network developed by Medtronic, Inc., of Minneapolis, MN, or some other network linking patient 14 to a clinician. PD 16 may spontaneously transmit information to the network or in response to an interrogation request from a user.

Power source 102 may be any type of device that is configured to hold a charge to operate the circuitry of PD 16. Power source 102 may be provided as a rechargeable or non-rechargeable battery. In other examples, power source 102 may incorporate an energy scavenging system that stores electrical energy from movement of PD 16 within patient 14.

Communication circuitry 94 includes any suitable hardware, firmware, software or any combination thereof for communicating with another device, such as device 21 or ICD system 30 (FIG. 1). Under the control of processing circuitry 90, communication circuitry 94 may receive downlink telemetry from and send uplink telemetry to device 21 with the aid of an antenna, which may be internal and/or external. Processing circuitry 90 may provide the data to be uplinked to device 21 and the control signals for the telemetry circuit within communication circuitry 94, e.g., via an address/data bus. In some examples, communication circuitry 94 may provide received data to processing circuitry 90 via a multiplexer.

Communication circuitry 94 may include circuitry that enables communication with another medical device, such as TCC or other types of communication. Communication circuitry 94 may operate for transmitting and/or receiving signals via switching module 91 and electrodes 52 and/or 60. When configured in a receiving or "listening" mode, communication circuitry may be powered up or enabled to allow signals to be detected or received. For example, communication circuitry may power one or more amplifiers in order to detect relatively weak signals that may be present in TCC. Powering these amplifiers, or otherwise operating communication circuitry to detect transmitted signals, consumes power. Therefore, communication circuitry 94 may employ communication schemes described herein that coordinate communication with a transmitting device in order to limit the amount of time that communication circuitry 94 is powered.

In one example, PD 16 may operate in a passive, or slave mode, to communicate with a master transmitting device such as ICD system 30. In concert with the transmission schedule of ICD 9, PD 16 may be independently enabling and disabling communication circuitry 94 according to a communication schedule. PD 16 may initiate a communication window during which PD 16 is capable of receiving the control signal from ICD 9, the communication window being one communication window of a plurality of communication windows defined by a communication schedule that corresponds to the transmission schedule. PD 16 is generally not capable of receiving the control signal between the plurality of communication windows. After PD 16 receives, from ICD 9 and during the communication window, the control signal, PD 16 may then schedule delivery of the therapy at the time according to the control signal and deliver the therapy at the time. In this manner, PD 16 may be configured to deliver a pacing pulse to the left ventricle, for example, according to the commands provided by ICD 9 via the control signal. In this manner, PD 16 may not be required to include sensing circuitry for sensing cardiac signals. However, in other examples, PD 16 may still be configured to sense cardiac events as a further check before delivering pacing pulses or to provide back-up pacing in the event that communication from ICD 9 has been lost. PD 16 may also communicate with other medical devices, in either the master or slave capacity.

From the perspective of PD 16, the control signal provides information regarding when to deliver therapy (e.g., a pacing signal) to the patient. For example, the control signal may indicate a delay period between receiving the control signal and the time at which PD 16 is to deliver the therapy to the patient. PD 16 can use this delay in order to schedule or program the therapy delivery, such as how to time when to deliver a pacing signal. In this manner, the control signal may provide information in code that PD 16 translates using a lookup table or formula. If the control signal is digital, PD 16 may use a portion of the control signal for timing the subsequent therapy. For example, if a typical control signal includes seven bits, PD 16 may time the therapy off of the last bit of the signal.

As a part of the communication schedule, PD 16 may incorporate a blanking window to reduce unnecessary powering of communication circuitry 94 when no signals from the transmitting master device are expected. For example, responsive to receiving the control signal indicating when to deliver therapy, PD 16 may initiate a blanking window during which PD 16 does not initiate any communication windows of the plurality of communication windows. PD 16 may continue to track communication windows that would otherwise have occurred during the blanking window. In other examples, PD 16 may cease tracking communication windows during the blanking window. Once PD 16 determines that the blanking window has elapsed, PD 16 may, responsive to determining that the blanking window has elapsed, initiate a next communication window according to the communication schedule. The blanking window may be adaptive based on the heart rate of the patient such that the blanking window increases for decreasing heart rates and the blanking window decreases for increasing heart rates. Any change in blanking window may be directed by a specific signal from the master device, by the slave device in response to detecting changes in the heart rate, or made based on when the synchronization signal is detected from the master device.

The communication window may generally be longer than the duration of time it would take PD 16 to receive a transmission from the master device. Moreover, the communication schedule of PD 16 may be aligned, or synchronized, with the transmission schedule of the master device such that each transmission window would occur in the middle of the respective communication window. In this manner, small deviations between the independently controlled transmission and communication schedules that may be due to differences in clock signals, for example, may not prevent each transmission from still being captured during the respective communication window. For example, PD 16 may initiate the communication window by starting the communication window prior to an expected transmission window of the transmission schedule, the communication window continuing for a duration of time that includes the expected transmission window.

In some examples, PD 16 may, responsive to receiving the control signal, immediately terminate the communication window by disabling communication circuitry 94. Although the communication window may be scheduled to continue beyond reception of the control signal, communication circuitry 94 does not need to be powered because no further signals will be received. Therefore, PD 16 can further reduce power consumption by terminating the communication window and powering down communication circuitry 94 immediately following reception of the transmitted signal. Further, PD 16 may align, or synchronize, the communication schedule to transmission windows based on when a control signal is received during the communication window. For example, PD 16 may, based on when the control signal is received, alter at least one of a starting time of a subsequent communication window or a window duration of the subsequent communication window to align the communication schedule and the transmission schedule to capture a subsequent control signal.

In other words, PD 16 may shift the communication schedule forward or backward such that expected transmissions will fall in the middle of a respective communication window for PD 16. These adjustments may be made to accommodate differences in clock speeds, or unstable clock speeds, that occur between the communication medical devices. Alternative to moving the communication schedule, PD 16 may also generate a clock signal correction factor that speeds up (increases) or slows down (decreases) the clock signal if PD 16 in an attempt to match the clock speed of the master device. For example, the clock signal correction factor may multiply the clock signal by the clock signal correction factor in order to generate a clock that attempts to replicate the clock of the transmitting device (e.g., ICD 9) such that the transmission schedule and communication schedule are aligned in time. In this manner, PD 16 may generate, based on when the control signal is received, the clock signal correction factor that corrects for the difference between when the control signal was received and an expected time for receiving the control signal from ICD 9. PD 16 may then apply the clock signal correction factor to the clock signal of the PD 16 to temporally align the communication schedule with the transmission schedule.

PD 16 may also increase or decrease the duration of each communication window in order to attempt to ensure that the transmitted signals are captured by PD 16. In one example, PD 16 receives the control signal within a predetermined percentage of one of a start or an end to the communication window, and, responsive to receiving the control signal within the predetermined percentage of one of the start of the end of the communication window, PD 16 may lengthen the window duration of the subsequent communication window. In other words, PD 16 may increase the length of the communication window if the transmitted signals are being received too close to the start or end of the communication window.

In some examples, PD 16 may decrease the length of the communication window and the time that communication circuitry 94 is actively listening for signals when the communication windows can be smaller. For example, PD 16 may receive the control signal within a predetermined percentage of an expected time for receiving the control signal, such as the middle of the communication window, and, responsive to receiving the control signal within the predetermined percentage of the expected time for receiving the control signal, shortening the window duration of the subsequent communication window. The amount of lengthening or shortening of the communication window may be relatively small, such as changing the length of the communication window by 5 percent or 10 percent or by a certain period of time such as 1 ms or 2 ms. However, this process may be performed iteratively. In addition, the amount of change in the communication window duration may be determined based on a running average or other historical information indicating the extent of any variation between the transmission schedule of the master device and the communication schedule of the slave device.

Each communication window of the plurality of communication windows may occur at a predetermined rate or predetermined interval. For example, the predetermined rate of the communication windows may be approximately 10 Hz to approximately 50 Hz. A predetermined interval corresponding to this rate may be used in different examples. The predetermined interval may be measured between the start of each window or from the end of one window to the beginning of the next window. In one example, the communication windows may have a rate of approximately 20 Hz or an interval that corresponds to this rate. However, different frequencies may be used in other examples. In some examples, the plurality of communication windows occur at a rate and with a duration such that the communication windows, or the time during which communication circuitry 94 is active, is less than two percent of a duty cycle of the entire communication schedule. In other words, for a 1 second period of time, the communication circuitry 94 may only be active or powered for less than about 20 ms.

As discussed herein, PD 16 may provide different types of therapy. In some examples, PD 16 is configured to be implanted within a left ventricle of a heart of the patient, but PD 16 may alternatively be placed in other chambers as well. PD 16 may be configured to provide left ventricle pacing signals, alone or in combination with other devices providing pacing to different chambers or structures of the heart.

In some situations, communication between the master device (e.g., ICD system 30) and the slave device (e.g., PD 16) may not be reliable. For example, in the case of TCC, the transmitted electrical signals may be provided in an environment with many other electrical signals, physiological and/or artificial, that create a very noisy environment that prevents consistent detection of the transmitted signals by PD 16. In other examples, the clocks of ICD system 30 and PD 16 may vary to a large extent, or due to some other error, such that PD 16 misses control signals requesting therapy delivery. After a lack of synchronizing for a predetermined period of time (e.g., from 1 second to 6 seconds or more), PD 16 may determine that a loss of communication has occurred. In these situations, PD 16 may initiate independent physiological testing in order to detect cardiac events and provide therapy without instruction from the master device. For example, PD 16 may provide backup VVI pacing when communication has been lost. PD 16 may cease this backup pacing upon re-synchronization of the communication with the master device such as ICD system 30.

When communication has been lost, PD 16 may attempt to adjust the communication schedule in order to re-detect signals from the master device. In one example, PD 16 may iteratively increase the duration of communication windows until a PD 16 detects a synchronization signal or a control signal. Upon re-establishing communication, PD 16 may revert to the previous communication schedule. In other examples, PD 16 may turn on communication circuitry 94 continuously until communication can be re-established with the master device.

Figure 6:
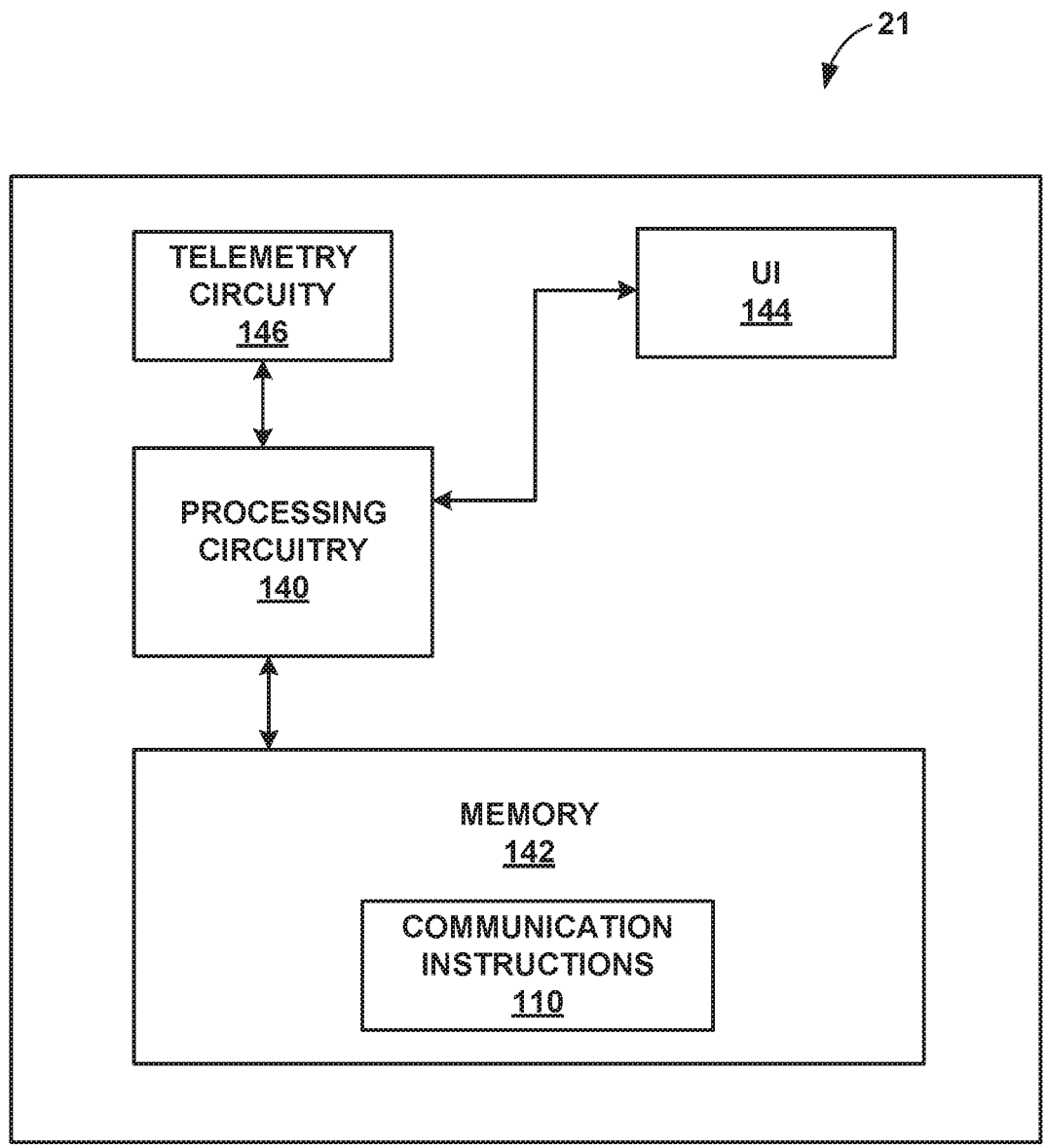
FIG. 6 is a functional block diagram illustrating an example configuration of the external device of FIG. 1 in accordance with one or more aspects of the present disclosure.

FIG. 6 is a functional block diagram of an example configuration of external device 21. In the example of FIG. 6, external device 21 includes processing circuitry 140, memory 142, user interface (UI) 144, and telemetry circuitry 146. External device 21 may be a dedicated hardware device with dedicated software for the programming and/or interrogation of one or more devices within cardiac system 8, including either PD 16 or IMD 30. Alternatively, external device 21 may be an off-the-shelf computing device, e.g., running an application that enables external device 21 to program and/or interrogate devices within cardiac system 8.

In some examples, a clinician or user uses external device 21 to select or program values for operational parameters of devices within cardiac system 8, e.g., for cardiac sensing, therapy delivery, and disabling and/or enabling PD 16. In some examples, a clinician uses external device 21 to receive data collected by devices within system 8, such as information about the condition of ICD system 30, including information relating to remaining battery life. External device 21 may also receive data from PD 16, including whether it delivery therapy is currently enabled or not. External device 21 may also receive other operational and performance data of devices within cardiac system 8.

The user may interact with external device 21 via UI 144, which may include a display to present a graphical user interface to a user, and a keypad or another mechanism for receiving input from a user. External device 21 may communicate wirelessly with one or more devices within system 8 using telemetry circuitry 146, which may be configured for RF communication with communication circuitry 94 of PD 16 or communication circuitry 80 of ICD 30. Any appropriate communication protocols beyond RF communication may be used.

Processing circuitry 140 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 106 may include multiple components, such as any combination of one or more microprocessors, one or more DSPs, one or more ASICs, or one or more FPGAs, as well as other discrete or integrated logic circuitry, and/or analog circuitry.

Memory 142 may store program instructions, such as communication instructions 110, which may include one or more program modules, which are executable by processing circuitry 140. When executed by processing circuitry 140, such program instructions may cause processing circuitry 140 and external device 21 to provide the functionality ascribed to them herein. The program instructions may be embodied in software, firmware and/or RAMware. Memory 142 may include any volatile, non-volatile, magnetic, optical, or electrical media, such as a random access memory (RAM), read-only memory (ROM), non-volatile RAM (NVRAM), electrically-erasable programmable ROM (EE-PROM), flash memory, or any other digital media.

A clinician may use external device 21 in FIG. 6 to communicate with PD 16 and/or ICD 9, and thereby enable or disable delivery of therapy in accordance with one or more aspects of the present disclosure. In addition, external device 21 may communicate with PD 16 and/or ICD 9 to program or update communication schedules. External device 21 may communicate using RF directly to various devices, and in some examples, provide instructions via RF to one device (e.g., ICD 9) and instruct that device to relay instructions to another device (e.g., PD 16) via TCC. As described below, a clinician may also perform an assessment of devices within cardiac system 8 and use external device 21 to modify or update parameters stored within PD 16 or other devices within cardiac system 8 (such as ICD 9). Communication instructions 110 may include communication schemes used by various transmitting and/or receiving devices that use TCC or any other modality to communicate as described herein. For example, communication instructions 110 may include instructions for each transmitting device (e.g., master device) and receiving device (e.g., slave device) regarding the transmission and communication schedules such as rate of windows, duration of time that communication circuitry is active, blanking windows, error handing, or any other aspect of communication such as those discussed herein. In some examples, external device 21 may provide user selectable parameters via UI 144 and update one or more aspects of communication instructions 110 based on input received from the user via UI 144.

Figure 7:
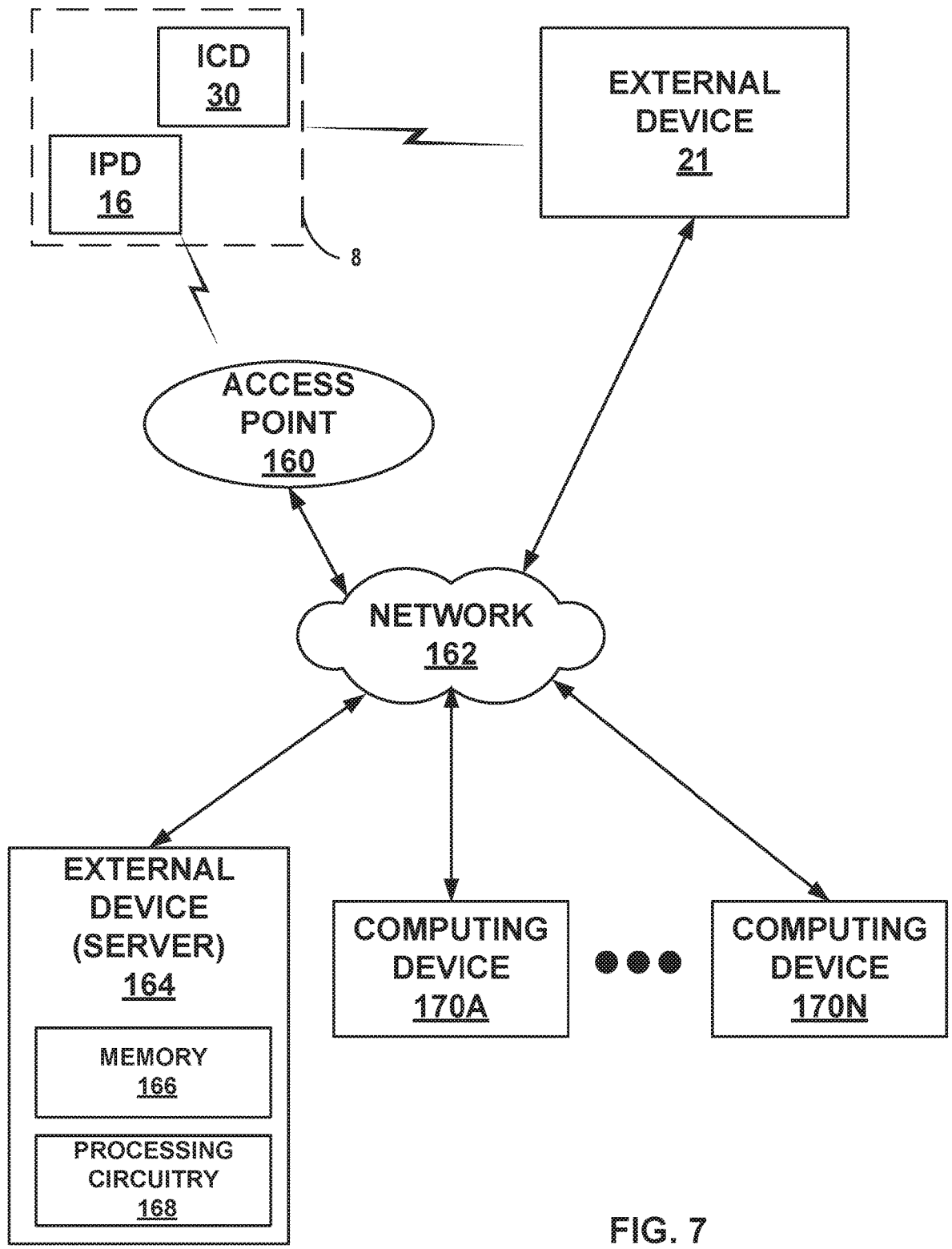
FIG. 7 is a functional block diagram illustrating an example network including the external device of FIG. 1 in accordance with one or more aspects of the present disclosure.

FIG. 7 is a functional block diagram illustrating an example system that includes external computing devices, such as a server 164 and one or more other computing devices 170A-170N, that are coupled to devices within cardiac system 8 (including PD 16 and ICD system 30) and external device 21 via a network 162. In this example, PD16 may use communication circuitry 94 to, e.g., at different times and/or in different locations or settings, communicate with external device 21 via a first wireless connection, and to communicate with an access point 160 via a second wireless connection. Similarly, ICD system 30 may use communication circuitry 80 to, e.g., at different times and/or in different locations or settings, communicate with external device 21 via a first wireless connection, and to communicate with an access point 160 via a second wireless connection. In the example of FIG. 7, access point 160, external device 21, server 164, and computing devices 170A-170N are interconnected, and able to communicate with each other, through network 162.

Access point 160 may comprise a device that connects to network 162 via any of a variety of connections, such as telephone dial-up, digital subscriber line (DSL), or cable modem connections. In other examples, access point 160 may be coupled to network 162 through different forms of connections, including wired or wireless connections. In some examples, access point 160 may be co-located with patient 14. Access point 160 may interrogate devices within the cardiac system 8, e.g., periodically or in response to a command from patient 14 or network 162, to retrieve information such as operational data from devices within cardiac system 8. Access point 160 may provide the retrieved data to server 164 via network 162. In accordance with one or more aspects of the present disclosure, a clinician may use external device 21 in FIG. 7 to communicate with PD 16, and thereby enable or disable delivery of therapy, and in some examples, modify or update parameters stored within PD 16 or other devices within cardiac system 8, such as the communication schedules and transmission schedules being used by the devices.

In some cases, server 164 may be configured to provide a secure storage site for data that has been collected from one or more devices within cardiac system 8 and/or external device 21, such as the Internet. In some cases, server 164 may assemble data in web pages or other documents for viewing by trained professionals, such as clinicians, via computing devices 170A-170N. The illustrated system of FIG. 7 may be implemented, in some aspects, with general network technology and functionality similar to that provided by the Medtronic CareLink® Network developed by Medtronic plc, of Dublin, Ireland.

Figure 8A:
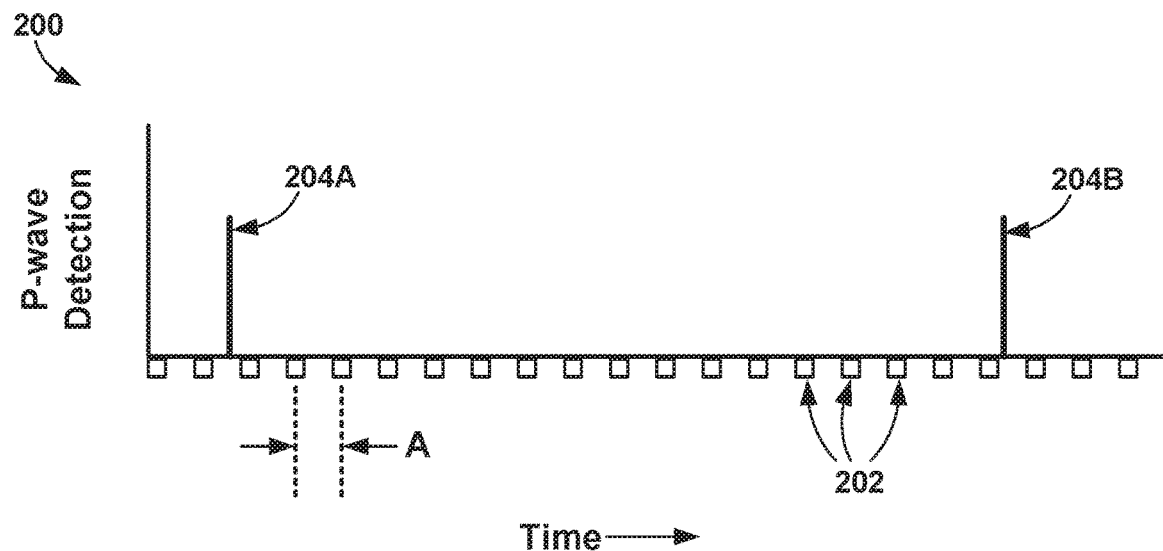
FIGS. 8A and 8B are timing diagrams of example cardiac event detection and control signal transmission from a medical device.
Figure 8B:
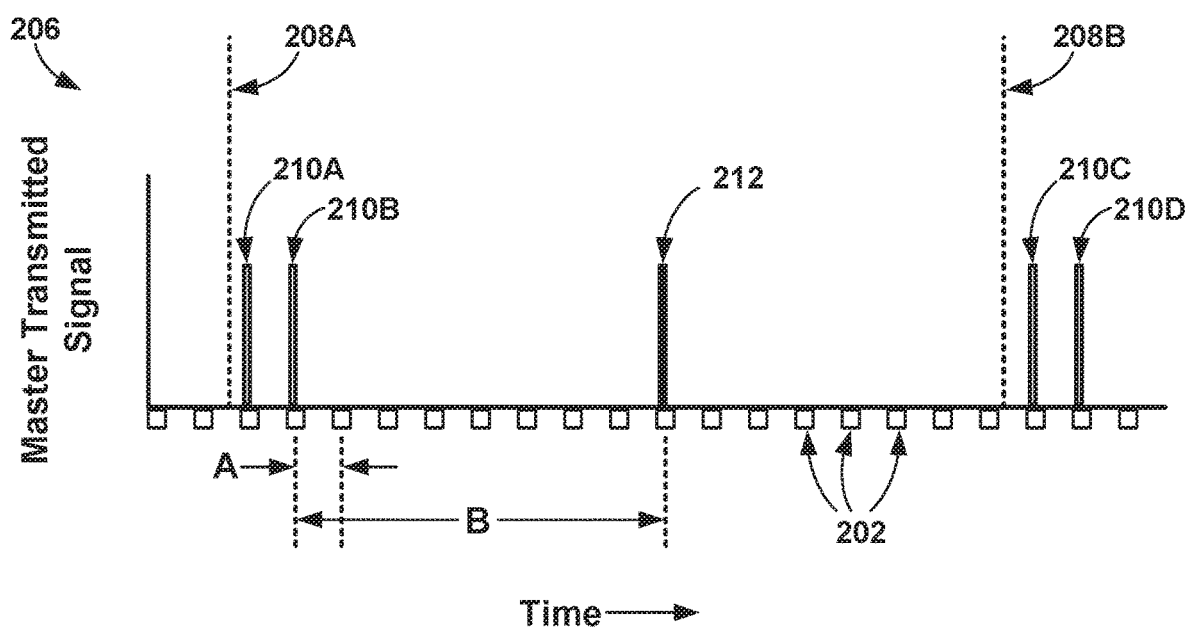

FIGS. 8A and 8B are timing diagrams of example cardiac event detection and control signal transmission from a medical device. FIGS. 8A and 8B will be described with respect to a master device (e.g., ICD system 30) and a slave device (e.g., PD 16), but other devices could be used in other examples. As shown in FIG. 8A, timing diagram 200 shows example detection of a cardiac event, such as P-waves 204A and 204B. Each of P-waves 204A and 204B are from respective cardiac cycles and are indicative of atrial contractions. Interval A indicates the interval of time between each transmission window of transmission windows 202. Transmission windows 202 occur at predetermined times, so the sensed P-waves 204A and 204B may not coincide with any transmission window. However, this does not affect the communication between ICD system 30 and PD 16. ICD system 30 may detect each P-wave 204A and 204B as cardiac events and then determine when PD 16 should deliver a corresponding pacing signal, for example, based on these detected cardiac events.

As shown in timing diagram 206 of FIG. 8B, ICD system 30 generates control signals 210A-D based on the cardiac events 208A and 208B that correspond to the detected P-waves 208A and 208B in FIG. 8A. ICD system 30 determines that cardiac event 208A occurred in time and also determines that the corresponding pacing signal should be delivered to the patient at a later time. ICD system 30 determines that the next transmission window occurs and generates a control signal 210A based on the timing of that transmission window and the time at which therapy should be delivered by PD 16. For example, if a pacing signal should be delivered 90 ms after control signal 210A is transmitted, then control signal 210A will indicate that the pacing signal should be delivered in 90 ms. If the interval A is less than the delay to the therapy, which would be the case if interval A is 50 ms, then ICD system 30 generates a second control signal 210B for transmission during the next transmission window and that indicates the therapy should now be delivered in 40 ms. Since the transmission window after control signal 210B is later than the delivered therapy, ICD system 30 cannot again transmit a control signal for that respective pacing signal. Therefore, ICD system 30 may begin blanking window B that runs for a predetermined time and typically covers multiple transmission windows. During blanking window B, ICD system 30 will refrain from transmitting any signals to PD 16.

At the termination of blanking window B, ICD system 30 transmits synchronization signal 212 during the very next transmission window after termination of the blanking window B. As discussed in FIG. 11, PD 16 may start or adjust the communication schedule in response to receive synchronization signal 212. Again, after ICD system 30 detects cardiac signal 208B, ICD system 30 will generate control signals 210C and 210D with different delay periods before the time of therapy delivery and for transmission during respective transmission windows. For example, since cardiac event 208B occurred earlier in time in relation to the transmission schedule than cardiac event 208A, the delay of control signals 210C and 210D may be 70 ms and 20 ms, respectively, between the transmission of the respective control signals and the therapy delivery. The interval and rate values provided in this example are merely used for illustration, and alternative values may be used in other examples.

In some examples, synchronization signal 212 may include a burst of two or more synchronization signals once the blanking window B has terminated or expired. This burst of synchronization signals may occur during a synchronization window and allow for the receiving device (e.g., PD 16) to detect at least one of the synchronization signals after the blanking window B even if the clock signals of the transmitting device (ICD system 30) and receiving device (PD 16) are slightly offset (e.g., each clock signal does not keep the exact same time). For example, instead of one synchronization signal, ICD system 30 may generate and transmit five synchronization signals separated by a predetermined interval (e.g., 2 ms) or at a predetermined rate (e.g., 500 Hz), with the middle synchronization signal in time transmitted at the planned termination of blanking window B. In other examples, the burst of synchronization signals may include two or more synchronization signals that are transmitted during a standard transmission window of the transmission schedule. However, in other examples, the burst of synchronization signals may be transmitted over a window longer than the standard transmission window in order to accommodate all of the synchronization signals of the burst. The synchronization rate that defines the rate of synchronization signals within the burst may be greater than the rate of the transmission windows within the transmission schedule. In this manner, synchronization signals will be transmitted during an error period before and after the expected termination of blanking window B at which time PD 16 would expect to receive a synchronization signal.

As tracked independently by PD 16, in response to the blanking window B ending, PD 16 may initiate a communication window during which PD 16 can detect signals from ICD system 30. If the clock signal of PD 16 is slow, PD 16 may still start the communication window early enough to capture at least one of the synchronization signals transmitted from ICD system 30. If the clock signal of PD 16 is fast, PD 16 may initiate the communication window and turn on the communication circuitry prior to the first synchronization signal. PD 16 may leave the communication window open until a synchronization signal is detected, and then terminate the communication window in response to detecting the first synchronization signal. PD 16 may then look for a subsequent synchronization signal that would be part of the synchronization signals transmitted at the end of blanking window B. Once PD 16 does not detect any further synchronization signals at the short intervals expected for the synchronization signals, PD 16 then resumes the normal communication schedule looking for transmitted signals during transmission windows 202, for example. PD 16 may use the last detected synchronization signal as the starting point for synchronizing the communication schedule to the transmission schedule of ICD system 30.

Figure 9:
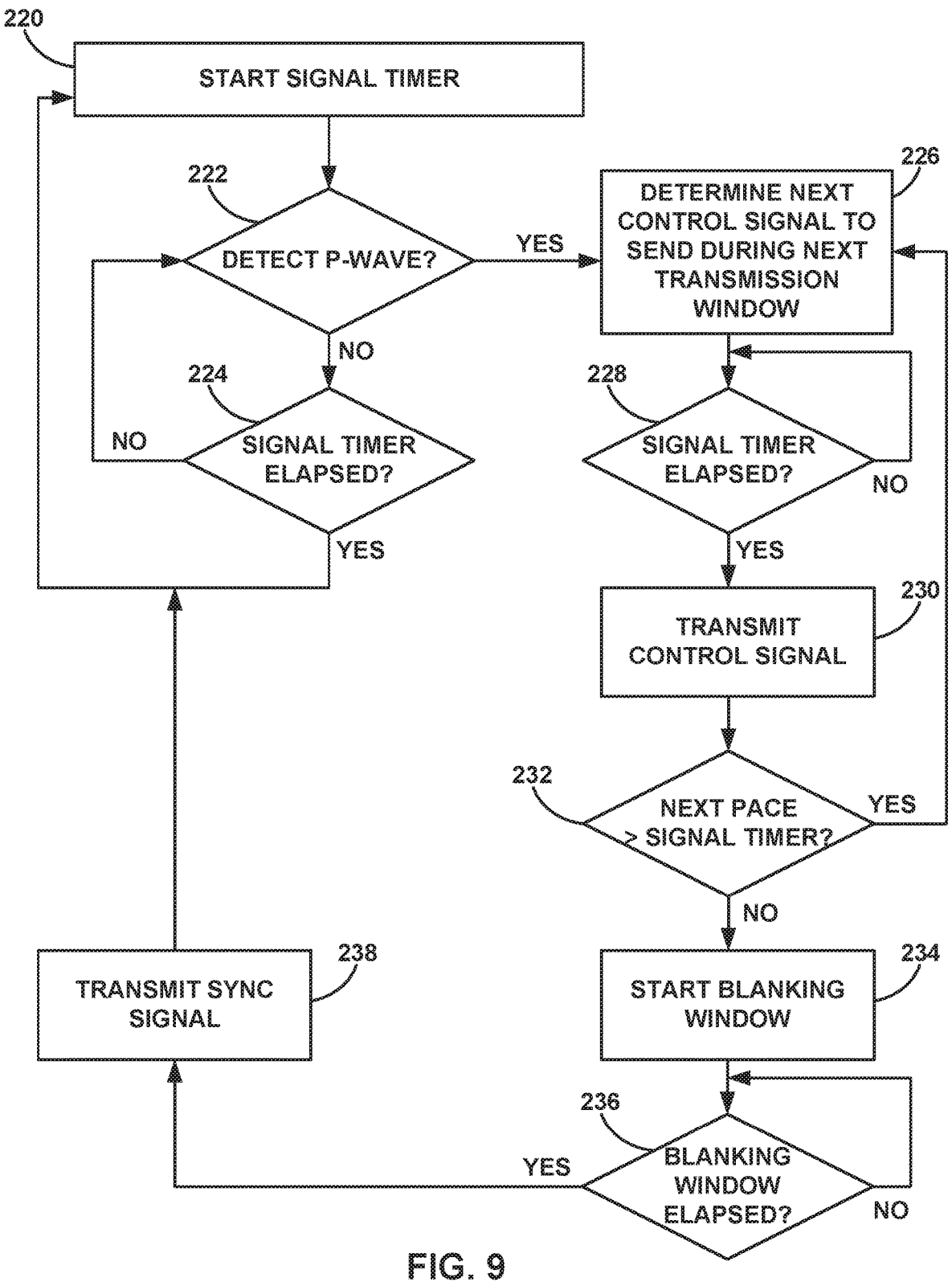
FIG. 9 is a flow diagram illustrating an example process for transmitting control signals according to a transmission schedule.

FIG. 9 is a flow diagram illustrating an example process for transmitting control signals according to a transmission schedule. For purposes of illustration, FIG. 9 is described below within the context of operations performed by processing circuitry 70 and communication circuitry 80 of ICD system 30 of FIG. 1 and FIG. 4, but the operations illustrated by the example of FIG. 9 may be performed by any medical device configured to operate as a master device in one-way communication. FIG. 9 is also described in relation with FIGS. 8A and 8B and in the context of sensing P-waves as cardiac events and requesting therapy in the form of a pacing signal delivered by the slave device (e.g., PD 16).

As shown in FIG. 9, processing circuitry 70 may start the signal timer, which is defined by the transmission schedule and times the intervals between each transmission window (220). If processing circuitry 70 does not detect a P-wave ("NO" branch of block 222), processing circuitry 70 determines whether or not the signal timer has elapsed, indicating that the interval between transmission windows has ended (224). If the signal timer has not elapsed ("NO" branch of block 224), processing circuitry 70 continues to determine if a P-wave has been detected (222). If processing circuitry 70 determines that the signal timer has elapsed ("YES" branch of block 224), processing circuitry 70 may restart the signal time (220).

If processing circuitry 70 determines that a P-wave has been detected ("YES" branch of block 222), processing circuitry 70 determines the next control signal to send during the next transmission window (226). For example, processing circuitry 70 may set the delay period of the control signal instruction to be the time between the next transmission window and the desired time at which the therapy should be delivered. Processing circuitry 70 next waits for the signal timer to elapse (228) and then generates and transmits, via communication circuitry 80, the control signal that indicates when PD 16 should deliver the therapy (e.g., the pacing signal) (230). If the next therapy (e.g., pace) time is further in time than the duration of the signal timer ("YES" branch of block 232), processing circuitry 70 may again determine the next control signal to send (226).

If the therapy is to occur sooner in time than the expiration of the next signal timer ("NO" branch of block 232), processing circuitry 70 starts the blanking window (234). During the blanking window, processing circuitry 70 does not transmit any control signals or synchronization signals to PD 16. If the blanking window elapses ("YES" branch of block 236), processing circuitry 70 may generate and transmit, via communication circuitry 80, a synchronization signal to IPG 16 in order to facilitate synchronization of the transmission schedule and the communication schedule of the two devices (238). Processing circuitry 70 may then again start the signal timer which times the interval between each transmission window (220).

The signals generated and transmitted by the master device, e.g., ICD system 30, may be control signals that request delivery of therapy, synchronization signals for aligning the communication and transmission schedules in time, and other signals relevant to the operation of PD 16 with respect to ICD system 30. Each signal transmitted from ICD system 30 may represent a code that corresponds to a particular message. As shown in Table 1 below, different codes may provide messages indicating different delays between the transmission of the signal and the timing of the therapy delivery (e.g., the pace signal). The signals may be coded for other tasks such as synchronizing the communication, resetting a blanking window, or even changing between different modes of operation.

TABLE 1

| Code | Message |
|---|---|
| 0 | Pace now |
| 1 | Pace in 10 msec |
| 2 | Pace in 20 msec |
| 3 | Pace in 30 msec |
| 4 | Pace in 40 msec |
| 5 | Pace in 50 msec |
| 6 | Pace in 60 msec |
| 7 | Pace in 70 msec |

TABLE 1-continued

| Code | Message |
|---|---|
| 8 | Pace in 80 msec |
| 9 | Pace in 90 msec |
| 10 | Pace in 100 msec |
| 11 | Pace in 110 msec |
| 12 | Pace in 120 msec |
| 13 | Sync |
| 14 | Reset 400 msec Blanking Timer |
| 15 | Change to Program Mode |

The messages of Table 1 can be coded using different types of signals, such as analog or digital signals. In one example, each signal may be digital and contain a number of different bits for different purposes. A control signal may be more complicated than a sync message. The message of the control signal may be coded in 4 bits of information which would provide 16 different possible messages (which are shown in Table 1 above). More bits could be used to code a greater number of messages. However, a 7-bit code may be used in order to detect up to two-bit errors or correct one-bit errors for this 4-bits of information. These bits may follow a number of bit series used for various functions. Since the receiving device does not know when to expect the transmission, it will not be possible to determine where the edges of the bits occur. Therefore, a first series of bits will be sent as a "wake-up series" of bits. For example, every message could begin with the bit series "101010."

Since the receiver (e.g., PD 16) will likely miss a few bits of the wake-up series, a flag of a number of bit will be inserted after the wake-up series. This flag may be a 3-bit flag, for example, and provide a measurement purpose for timing of the transmitted signal. An example flag could be the bit series "011." In one example, the last bit of the flag may be used by the PD 16 to track timing of the transmitted signals. The message code may then follow the flag. Therefore, an example control signal may be "101010011" plus the 7 bits of the message. The sync signal could only include the wake-up series and the flag since the message would not be needed. These types of codes and the number of bits discussed herein are merely examples, and other codes, bits, arrangements of bits for "wake-up series," flags, and messages may be used in other examples consistent with the communication described herein.

The duration of each control signal may be dependent on the frequency of the communication protocol and the encoding scheme used. For example, a frequency shift keying (FSK) protocol, or a phase shift keying (PSK) protocol, or an amplitude modulated protocol (AM) may be used to send the signals from the master device. The FSK may be more tolerant to clock differences than other coding schemes. The FSK system may allow the receiver to synchronize more quickly with the start of the message than other coding schemes. The FSK protocol may also not require the long lock-in time associated with PSK protocols and achieve better noise rejection than AM protocols which may make the FSK protocol preferable for relatively short messages between devices. If an operational frequency is used where a bit is approximately 80 μsec long, the 16 bit message discussed above will take approximately 1.28 ms. Therefore, the communication window for detecting this message would need to be set long enough to capture the entire signal.

Although the process of FIG. 9 is directed to determining and transmitting a control signal to PD 16, ICD system 30 may generally transmit information related to the detected cardiac event. This information may include the control signal and/or other information such as a timing between the detected cardiac event and the transmission window. This information may specify an amount of time between when the cardiac event was detected and when the transmission window was scheduled. The timing between the cardiac event and the transmission window may be configured to allow PD 16 to determine a time to deliver the therapy based on when the cardiac event was detected. For example, processing circuitry 70 may determine this timing of the cardiac event within block 226 and then transmit the information instead of the control signal. PD 16 may then receive the information and determine when to deliver the therapy based on the amount of time that had elapsed between the detection of the cardiac event and the transmission of the information. In one specific example, PD 16 may subtract the time between the detected cardiac event and the transmission window from an A-V interval to determine the amount of time to wait prior to delivering a pacing signal. ICD system 30 may determine and transmit other information in this same manner to PD 16 in other examples.

Figure 10:
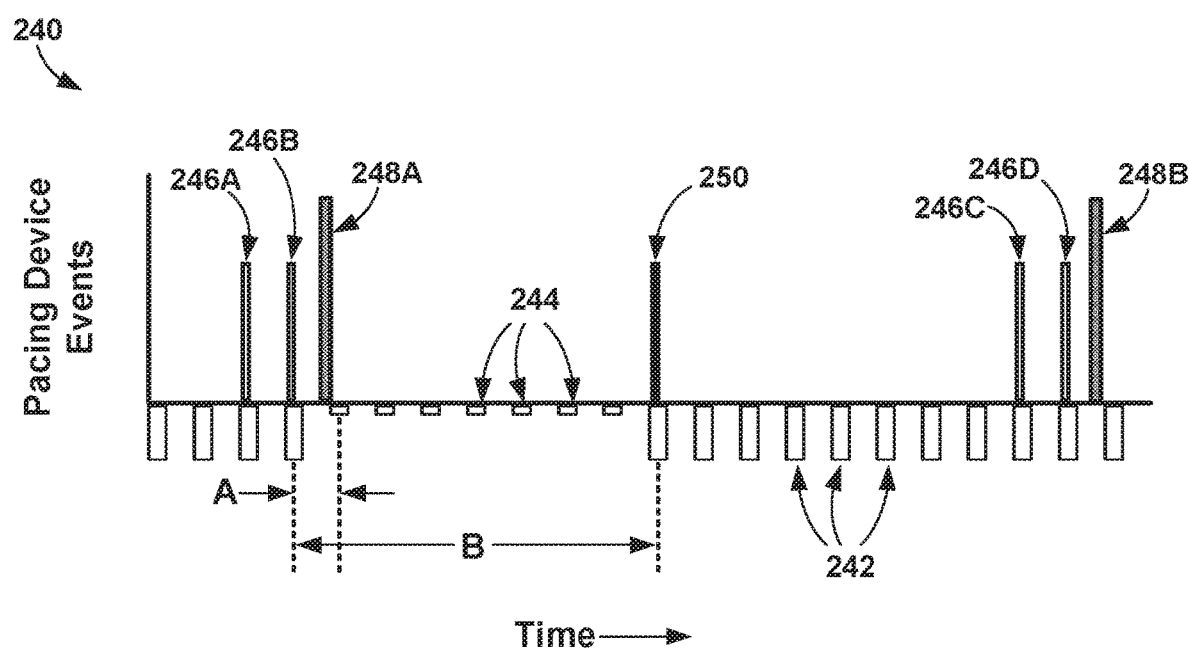
FIG. 10 is a timing diagram of example control signals received by an implantable medical device during respective communication windows of a communication schedule.

FIG. 10 is a timing diagram of example signals received by an implantable medical device during respective communication windows of a communication schedule. FIG. 10 will be described with respect to a master device (e.g., ICD system 30) and a slave device (e.g., PD 16), but other devices could be used in other examples. As shown in FIG. 10, timing diagram 240 shows example detection of signals from the master device and by the slave device of PD 16. Similar to FIGS. 8A and 8B, interval A indicates the interval of time between each communication window of communication windows 242. Communication windows 242 occur at predetermined times that correspond to expected transmission windows of ICD system 30.

Control signals 246A and 246B are received during respective communication windows 242 and correspond to the control signals 210A and 210B transmitted by ICD system 30 discussed in FIG. 8B. Each of control signals 246A and 246B define a respective delay from the time of each control signal to the time at which PD 16 should deliver pacing signal 248A to the left ventricle, for example. As discussed in FIG. 8B, if pacing signal 248A should be delivered 90 ms after control signal 246A is received, then control signal 246A will indicate that the pacing signal should be delivered in 90 ms. If the interval A is less than the delay to the therapy, which would be the case if interval A is 50 ms, then a second control signal 246B indicates the therapy should now be delivered in 40 ms. As long as PD 16 detects one of these two control signals 246A or 246B, PD 16 should be able to generate and deliver the pacing signal 248A at the appropriate time. Once PD 16 determines that no further control signals can be received before the delivered therapy PD 16 may begin blanking window B that runs for a predetermined time and typically covers multiple communication windows. During blanking window B, PD 16 will refrain from powering communication circuitry 94 in order to reduce power consumption during a time in which no signals would be received. Communication windows 244 are windows that would have occurred in the communication schedule without the blanking window B.

At the termination of blanking window B, PD 16 may again power up communication circuitry 94 in order to detect synchronization signal 250 that corresponds to the synchronization signal 212 transmitted from ICD system 30. PD 16 can then again power up communication circuitry 94 for the communication windows for detecting subsequent control signals 246C and 246D that correspond to control signals 210C and 210D transmitted by ICD system 30. In response to detecting at least one of control signals 246C and 246D, IPG 16 may deliver the pacing signal 258B according to the timing specified by each of control signals 246C and 246D. PD 16 and ICD system 30 may continue in this fashion as needed to deliver therapy to the patient. In another example, the duration of blanking window B may be adjusted by the average heart rate. That is, as the heart rate increases and the time between successive p-waves, 204A to 204B, decreases, ICD system 30 and/or PD 16 may shorten blanking window B by one or more intervals A (or some other duration of time). Likewise, if the heart rate decreases, ICD system 30 and/or PD 16 may increase blanking window B by one or more intervals A (or some other duration of time). Heart rate can be determined by both PD 16 and ICD system 30 in some examples. In another example, ICD system 30 may eliminate synchronization signal 250 entirely and rely on control signals 246A and 246B for setting the time to deliver the therapy and adjusting the clock of the PD 16 to synchronize with ICD system 30. In this example, ICD system 30 may not utilize a blanking window, but PD 16 may still utilize a blanking window to reduce power consumption. The interval and rate values provided in this example are merely used for illustration, and alternative values may be used in other examples.

Figure 11:
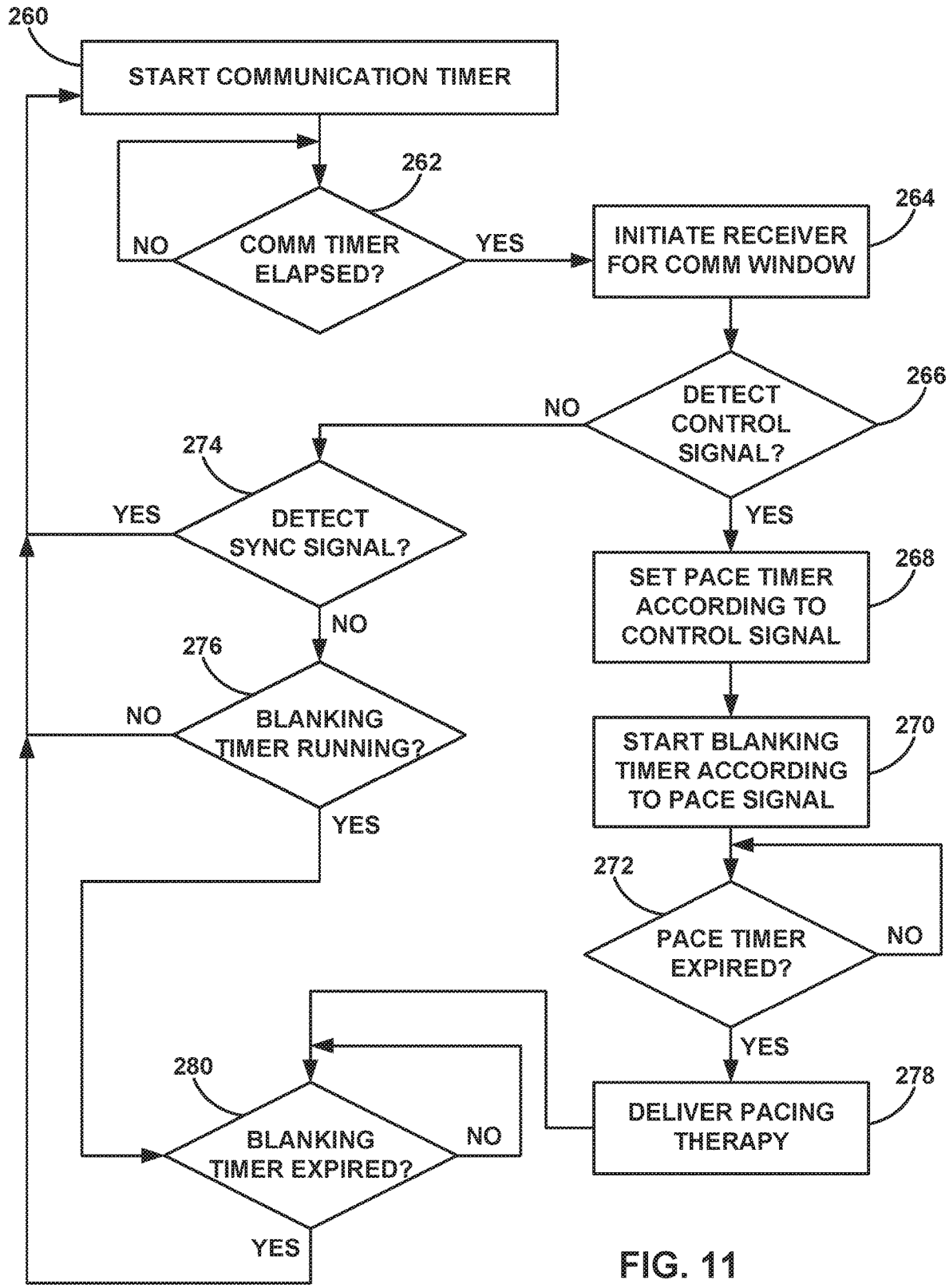
FIG. 11 is a flow diagram illustrating an example process for receiving control signals according to a communication schedule and delivering therapy based on the received control signal.

FIG. 11 is a flow diagram illustrating an example process for receiving control signals according to a communication schedule and delivering therapy based on the received control signal. FIG. 11 may be related to the signals generated as a result of the process of FIG. 9, and for purposes of illustration, FIG. 11 is described below within the context of operations performed by processing circuitry 90 and communication circuitry 94 of PD 16 of FIG. 1 and FIG. 5. However, the operations illustrated by the example of FIG. 11 may be performed by any medical device configured to operate as a master device in one-way communication, and possibly two-communications. FIG. 11 is also described in relation with FIG. 10 and in the context of delivering ventricular pacing signals by PD 16 (e.g., a slave device) in response to commands generated based on cardiac events such as P-waves detected by the master device (e.g., ICD system 30). Processing circuitry 90 is generally described as performing most of the process of FIG. 11, but these features may be performed by processing circuitry 90, communication circuitry 94, other circuitry of PD 16, or any combination thereof.

As shown in FIG. 11, processing circuitry 90 starts the communication timer which times the intervals from one communication window of the communication schedule to the next communication window (260). Processing circuitry 90 may wait until the communication timer elapses ("NO" branch of block 262). In response to determining that the communication timer has elapsed ("YES" branch of block 262), processing circuitry 90 may control communication circuitry 94 to initiate the receiver (or amplifier circuitry) for the communication window that starts at the expiration of the communication timer (264). Initiation of the receiver may include processing circuitry 90 closing a switch or otherwise directing power to the receiver amplification circuitry of communication circuitry 94 that allows PD 16 to detect signals from the master device (e.g., ICD system 30). Processing circuitry 90 may control the communication circuitry 94 to stay powered on for the duration of the communication window.

If processing circuitry 90 does not detect a control signal commanding therapy delivery ("NO" branch of block 266), processing circuitry 90 determines whether or not a synchronization signal has been detected (274). If the synchronization signal is detected ("YES" branch of block 274), processing circuitry 90 starts the communication timer to align the communication timer, and communication schedule, with the synchronization signal received from the master device (260). In some examples, processing circuitry 90 may use the received synchronization signal to schedule the start of the communication timer at a later time, as directed by instructions stored in memory 92. If processing circuitry 90 does not detect a synchronization signal ("NO" branch of block 274), processing circuitry 90 checks to determine if a blanking timer is running for a blanking window in which communication circuitry 94 should remain powered off (276). Processing circuitry 90 will start the communication timer if the blanking timer is not running ("NO" branch of block 276) or check to see if the blanking timer has expired if the blanking timer is running ("YES" branch of block 276).

Back to block 266, if processing circuitry 90 detects a control signal during the communication window ("YES" branch of block 266), processing circuitry 90 sets the pace timer according to the message of the control signal (268). In some examples, processor circuitry 90 may extend the duration of the communication window until the control signal is completely received. This situation may occur when the beginning of the control signal is received during the communication window, but the duration of the control signal would otherwise go beyond the scheduled duration of the communication window. Processing circuitry 90 may, upon detection of the control signal, automatically extend the communication window for a period of time that includes the expected duration of the control signal. In other examples, processing circuitry 90 may be configured to maintain operation of the receiver during receiving of the control signal and disable or turn off the receiver after a period of time elapses during which no further signal is detected. In this manner, processing circuitry 90, or other circuitry, may ensure that the full control signal is received even if the end of the control signal might occur after the end of the scheduled communication window.

As discussed herein, the control signal may indicate a delay between the transmission of the control signal and the desired time for delivery of the therapy. Processing circuitry 90 may schedule the pacing signal in the future at the duration of the delay indicated by the control signal, but processing circuitry 90 may apply a correction or offset to this delay to account for processing time or other scheduling delays that would otherwise shift the therapy away from the intended time indicated by the control signal. Processing circuitry 90 then starts the blanking timer according to when the pace signal will be delivered (270). The blanking timer prevents PD 16 from turning on communication circuitry when no transmitted signals are expected from ICD system 30. Processing circuitry 90 then waits for the pace timer to expire ("NO" branch of block 272) and control signal generator 96 to generate and deliver pacing therapy to the patient (e.g., the left ventricle) (278).

The blanking timer times the duration of the blanking window and may start immediately in response to starting the pace timer (268) or, in other examples, after the pacing therapy is delivered (step 278). Starting the blanking timer immediately upon setting the pace timer may cause PD 16 to miss receiving any additional control signals that could be sent before the therapy is delivered (because PD 16 does not turn on communication circuitry during the blanking window), such as if the communication window interval is shorter than the pace timer duration. This may be beneficial to conserve power when a second, and redundant, control signal is not necessary. However, in some examples, the blanking window can be set to start after the therapy is delivered to allow PD 16 to confirm the accuracy of the first control signal with the message from another control signal commanding delivery of the same therapy. In addition, receiving an additional control signal closer in time to when the pacing therapy is delivered may reduce any timing variability between the clock of ICD system 30 and PD 16. Once the blanking timer is started, processing circuitry 90 waits until the blanking timer expires ("NO" branch of block 280). Upon expiration of the blanking timer ("YES" branch of block 280), processing circuitry 90 starts the communication timer (260). In other examples, processing circuitry 90 may immediately initiate the receiver of communication circuitry 94 (264) upon the expiration of the blanking timer.

The transmission windows and communication windows described with respect to FIGS. 8A, 8B, and 10, the processes of FIGS. 9 and 11, have windows that generally maintain a constant interval. In other examples, the transmission windows and communication windows may increase in rate in anticipation of a "deliver therapy now" signal from the master device. For example, ICD system 30 and PD 16 may generally operate respective windows at a regular interval, such as 50 ms. However, this rate may be too slow, or infrequent, to support an appropriate therapy delivery command that instructs PD 16 to immediately deliver therapy. Instead, in response to detecting a cardiac event, such as a P-wave, ICD system 30 transmits a signal to PD 16 during the last regular transmission window before therapy should be delivered that instructs PD 16 to start high rate communication windows, or more frequent or longer duration "listening" by the communication circuitry than occurs during the regular communication window schedule. In some examples, ICD system 30 may start high rate transmission windows (that may each include one or more sync signals) in order to maintain synchronization during the lead up to the therapy delivery control signal. The high rate transmission windows may also be started in response to detecting the cardiac event. At the time that ICD system 30 desires to instruct PD 16 to deliver therapy, ICD system 30 will transmit a "deliver therapy now" control signal to PD 16. In response to transmitting the control signal, ICD system 30 may begin a blanking window. In addition, PD 16 may begin a blanking window after receiving the control signal and delivering the therapy (e.g., a pacing signal).

Although the process of FIG. 11 is described with respect to receiving a control signal, a similar process may be performed by PD 16 when receiving types of information other than the control signal. For example, the information may include timing information that indicates when ICD system 30 detected the cardiac event (e.g., a P-wave). Since this timing information may specify the timing of when the cardiac event was detected, but not when to deliver therapy, processing circuitry 90 may analyze the timing information and determine when to deliver therapy. This determination step may occur after block 266. Once processing circuitry 90 determines when to deliver the therapy, the rest of the process can continue as determined. In this manner, PD 16 may be configured to process information instead of merely performing an action instructed by a control signal.

Figure 12A:
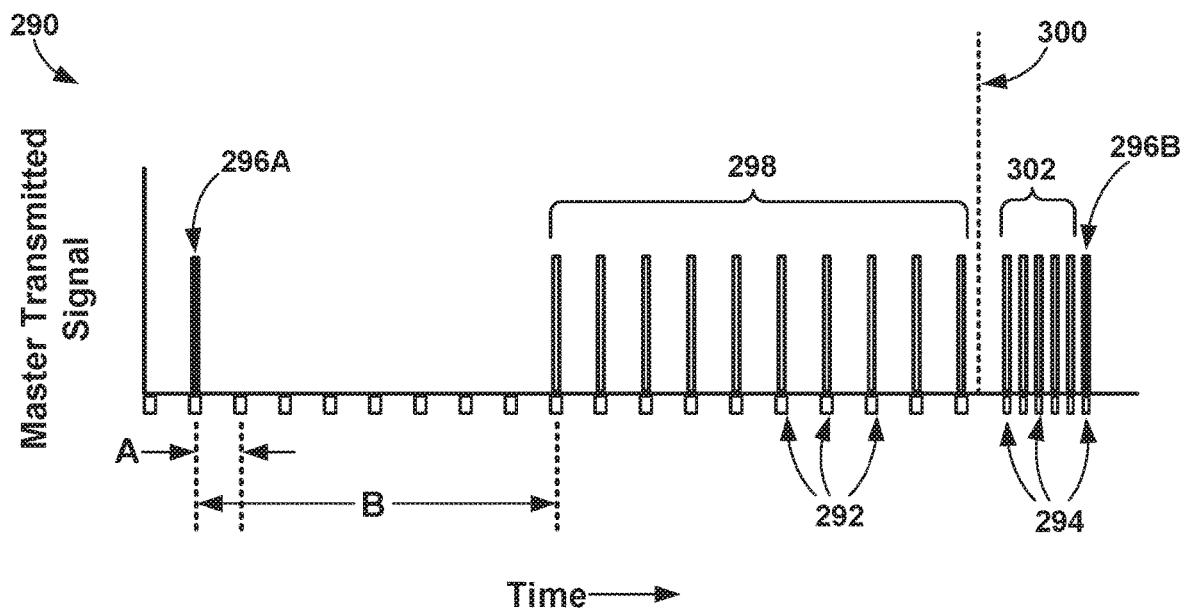
FIGS. 12A and 12B are timing diagrams of example control signal transmission from a medical device and control signals received by an implantable medical device.
Figure 12B:
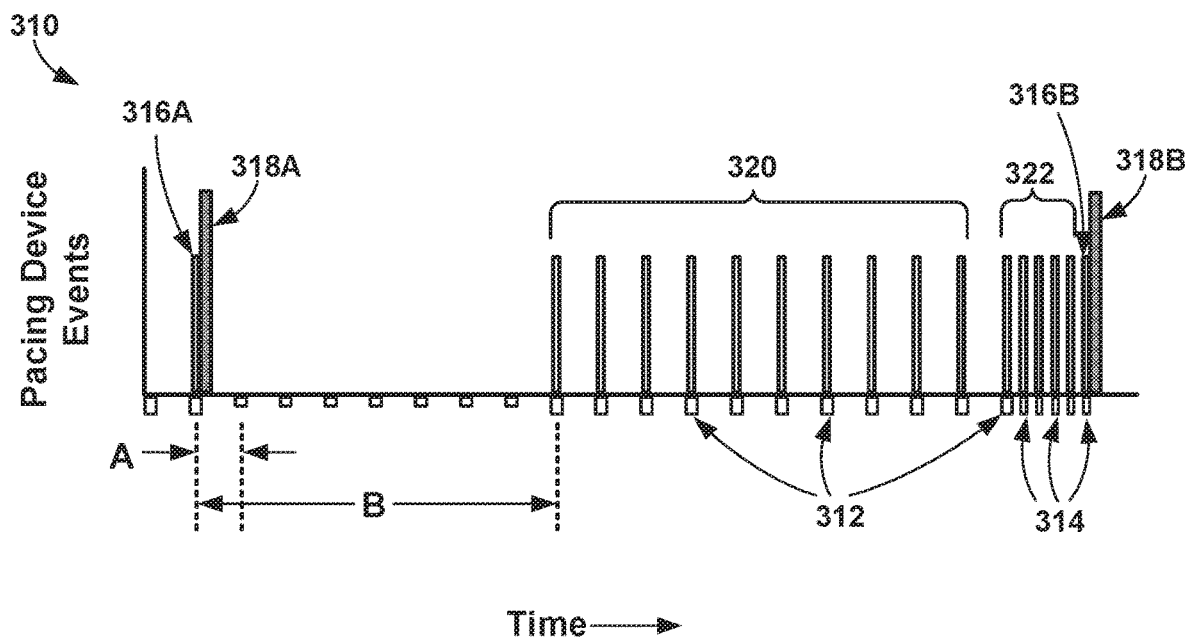

FIGS. 12A and 12B are timing diagrams of example control signal transmission from a medical device and control signal signals received by an implantable medical device. FIGS. 12A and 12B will be described with respect to a master device (e.g., ICD system 30) and a slave device (e.g., PD 16), but other devices could be used in other examples. FIG. 12A may be similar to the transmission of signals as described in FIG. 8B, and FIG. 12B may be similar to the receiving of signals as described in FIG. 10. However, the transmission schedule and communication schedule of FIGS. 12A and 12B adjust the rate of transmission and communication windows such that transmission periods are less frequent when control signals are likely not to occur and more frequent when control signals are more likely to be necessary, e.g., such as right before PD 16 is to deliver pacing signals.

As shown in timing diagram 290 of FIG. 12A, ICD system 30 detects cardiac events such as cardiac event 300 that may be a P-wave. ICD system 30 may also generate control signals 296A and 296B based on respective cardiac events that correspond to the detected P-waves. ICD system 30 determines that cardiac event 300 occurred in time and also determines that the corresponding pacing signal should be delivered to the patient at a certain time after the detected cardiac event. ICD system 30 may be configured to send synchronization signals 298 during transmission windows 292 that occur at a relatively slower rate (e.g., 20 Hz) and higher rate synchronization signals 302 during transmission windows 294. In this manner, ICD system 30 may limit communication to those periods of time right before PD 16 is to deliver pacing signals. FIG. 12B shows timing diagram 310 aligned in time with timing diagram 290 of FIG. 12A and indicates the received control signals and synchronization signals by PD 16 and delivered pacing signals 318A and 318B according to the control signals.

For example, ICD system 30 may deliver control signal 296A which indicates that PD 16 should deliver a pacing signal (e.g., a pacing pulse). In some examples, control signal 296A may instruct PD 16 to deliver the pacing signal as soon as possible or at some predetermined delay after transmission of the control signal 296A. Timing diagram 310, shows that PD 16 receives control signal 316A (the signal 296A from ICD system 30) and subsequently delivers pacing signal 318A. Interval A indicates the time between each of the transmission windows (e.g., transmission windows 292) of ICD system 30 and communication windows (e.g., communication windows 312) of PD 16. Immediately after transmitting control signal 296A, and after receiving control signal 316A, each respective device initiates blanking window B that runs for a predetermined time and typically covers multiple transmission windows and communication windows. During blanking window B, ICD system 30 will refrain from transmitting any signals to PD 16. Example durations for blanking window B may be 500 ms, for example, but other blanking windows may be shorter or longer. In some examples, the blanking window B may be adaptive and based on the detected length of the cardiac cycle of the patient such that longer blanking windows may be used for slower heart rates.

At the termination of blanking window B, ICD system 30 begins to transmit synchronization signals 298 during the very next transmission window after termination of the blanking window B. PD 16 may then receive the first corresponding synchronization signal 320 and start or adjust the communication schedule in response to receiving the first synchronization signal 320. In order to maintain synchronized schedules, ICD system 30 may continue to transmit synchronization signals 298 during each respective transmission window 292, and PD 16 will continue to turn on communication circuitry 94 in order to receive each of the synchronization signals 320. Alternatively, ICD system 30 may only deliver the first synchronization signal of synchronization signals 298, but PD 16 may still turn on communication circuitry 94 during each of communication windows 312.

During this time, ICD system 30 may sense for cardiac signals, such as a P-wave. Responsive to detecting cardiac event 300, ICD system 30 may increase the rate of the transmission schedule to include more frequent transmission windows 294 and control PD 16 to similarly increase the rate of the communication schedule. The first synchronization signal of synchronization signals 302 may indicate to PD 16 that the communication schedule should be changed to the higher rate. The first synchronization signal of synchronization signals 322 in timing diagram 310 is received by PD 16 and PD 16 changes the communication schedule to include more frequent communication windows 314. For example, transmission windows 294 and communication windows 314 may occur at a rate of 100 Hz (10 ms intervals) or 200 Hz (5 ms intervals), but lower or higher frequencies are also contemplated. Alternatively, ICD system 30 may only deliver the first synchronization signal of synchronization signals 302, but PD 16 may still turn on communication circuitry 94 during each of communication windows 314 until the control signal 316B is received during a communication window 314. In some examples, PD 16 may operate a time out period for the higher rate communication windows 314 such that if no control signal is received for a predetermined period of time, PD 16 reverts to less frequent communication windows. In this manner, PD 16 can conserve power if communication to ICD system 30 is interrupted or ICD system 30 does not transmit a control signal.

In some examples, each of synchronization signals 302 are provided to maintain synchronization of the transmission windows and communication windows between ICD system 30 and PD 16, respectively. When ICD system 30 determines that the pacing signal should be delivered after the next communication window 294, ICD system 30 may deliver control signal 296B that indicates PD 16 is to deliver the pacing signal. In response to receiving corresponding control signal 316B from ICD system 30, PD 16 may deliver pacing signal 318B. Control signal 296B transmitted by ICD system 30 may instruct the PD 16 to immediately deliver the pacing signal or identify a delay from the control signal before the pacing signal should be delivered. In other examples, some or all of synchronization signals 302 transmitted from ICD system 30 may indicate a respective delay to when the pacing signal is to be delivered. In this manner, synchronization signals 302 may provide a countdown for PD 16 to prepare for delivering the pacing signals. In addition, providing multiple signals that indicate the time at which PD 16 is to deliver the pacing signals allows for redundancy if one or more control signals are not detected by PD 16. After control signals 296B and 316B, each of ICD system 30 and PD 16 may again enter a blanking window (e.g., blanking window B).

Figure 13A:
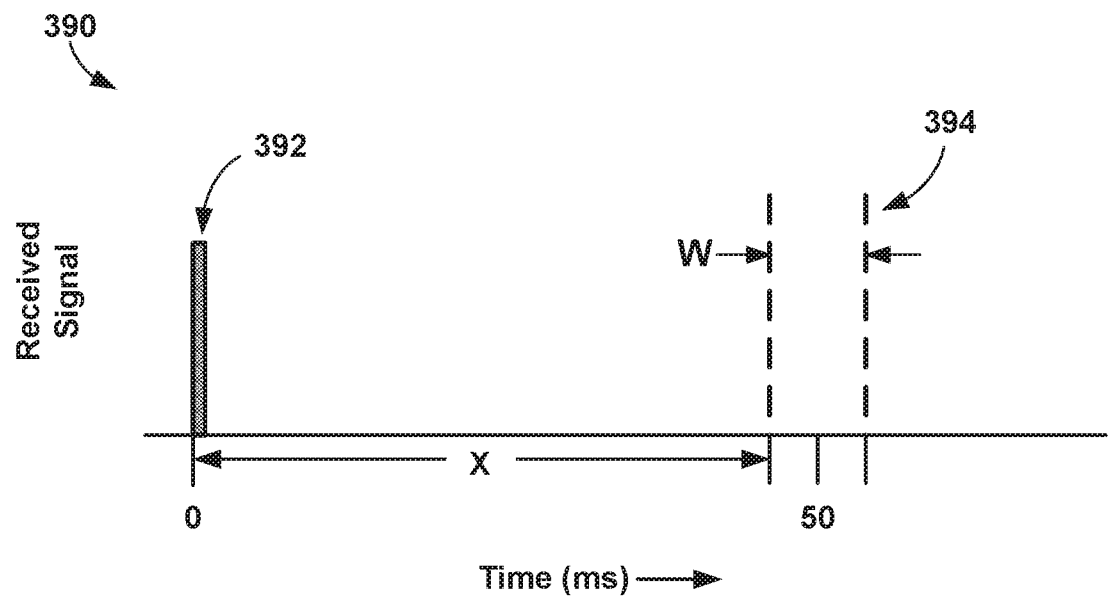
FIGS. 13A and 13B are timing diagrams indicating example reception of a control signal during a communication window.
Figure 13B:
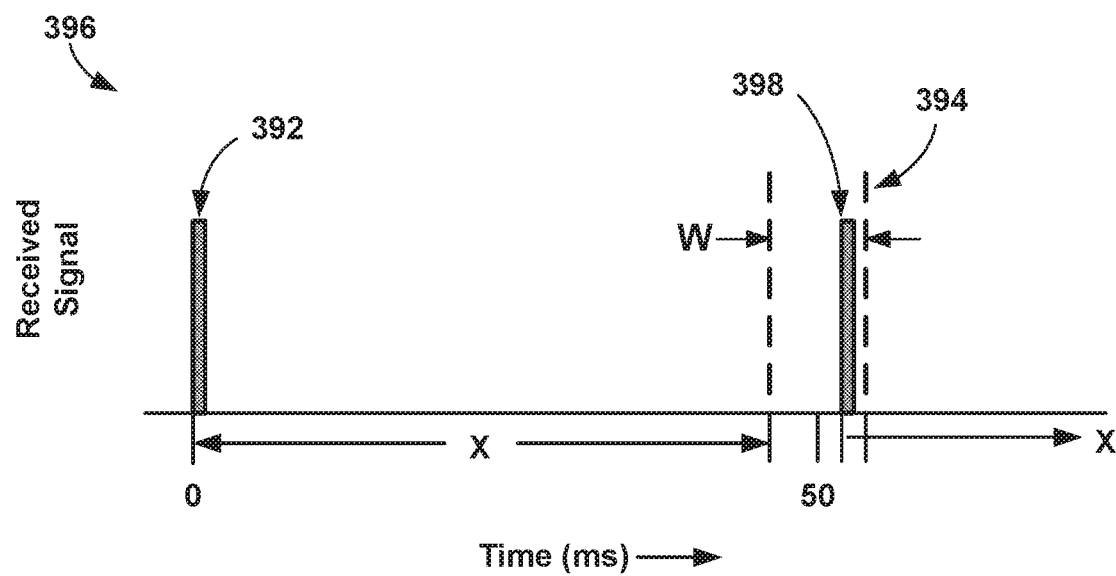

FIGS. 13A and 13B are timing diagrams indicating example reception of a control signal during a communication window determined by a receiving device, such as PD 16. In the example shown in FIG. 13A, the example interval between expected transmission windows is approximately 50 ms. In other words, if a transmitted signal 392 were received at time "0" (the start time of transmitted signal 392), the next expected transmitted signal would occur approximately 50 ms later in time from the start of transmitted signal 392. However, the control signals, or any other signals, transmitted by the master device (e.g., ICD system 30) may not always be received exactly at the time expected by PD 16. For example, the clock signal of PD 16 may vary slightly over time, be a little faster or a little slower than the clock of ICD system 30, or other transmission and reception delays can occur. Therefore, the communication window 394 may have a duration configured to receive signals that may deviate from the expected time. In addition, communication window 394 may be started at a time that provides the greatest opportunity to receive any transmitted signals.

Generally, communication window 394 may be timed such that the middle of the communication window 394 falls at the expected time to receive any transmitted signal. The expected time to receive the transmitted signal may be the start time for the transmitted signal, the expected time of the middle of the transmitted signal based on the expected duration of the transmitted signal, or the end time of the expected transmitted signal. Therefore, the middle of communication window 394 may be timed to fall at the interval, or rate of the communication schedule and the transmission schedule. The result is an interval X between the transmitted signal and the start of communication window 394. If no transmitted signal is received, the interval X may represent the time between the middle of the previous communication window, or in some cases, the end of the last communication window. The interval X may be timed by the communication timer. Interval X is also set by the desired width W of communication window 394. Communication circuitry 94 is enabled and "listening" for signals during the communication window 394. Therefore, communication window 394 may have a width W that is long enough to detect transmitted signals, but short enough such that communication circuitry 94 is not powered when no transmission signals will be sent. Width W may be set to a duration that is +/−a certain percentage of the interval X or a predetermined time, and width W may also be set to ensure that width W includes the duration of the expected control signal 398. For example, width W may be set to 3 ms, which would indicate that communication window W is open for 1 ms before and 1 ms after the expected transmission signal in addition to the expected 1 ms duration of the expected control signal 398. These durations of window W are merely examples, and the actual durations of width W and control signal 398 may be shorter or longer in other examples. In some examples, width W is set as a function of the expected variation between the clock of the transmitting device and the receiving device, the time since the last received signal, and the length of the signal transmission.

However, as shown in FIG. 13B, the transmitted control signal 398 may not be received exactly at the expected time. If the width W of communication 394 is large enough, communication circuitry 94 will still detect the control signal 398. Processing circuitry 90 may use the detected control signal 398 to synchronize the next communication window. Since the transmission windows should be scheduled at 50 ms intervals, processing circuitry 90 may start the communication timer that times the next interval at the time control signal 398 is received. In this manner, the interval X will run from the time control signal 398 was received to mitigate error between the clock signals from the transmitting and the receiving devices.

The width W may increase with the duration of time from the last configured signal that was received (transmitted signal 392). For example, if a transmitted signal is not detected, the receiving device may increase the width W to account for an increased potential error between the clock signals from the transmitting and receiving device. In addition, after blanking windows expire, the width W may be set to a duration that is larger to accommodate for possible clock variability during the blanking window. In some examples where the receiving device (e.g., PD 16) determines that it is no longer synchronized with the transmitting device (e.g., PD 16 has not detected a certain number of expected signals or a predetermined period of time has elapsed without receiving a signal), the width W may be extended indefinitely until a signal is detected or the receiving device determines that the transmitting device is no longer sending signals. In this manner, the width W may have a limited duration that would be greater than any expected time between consecutive signals (e.g., one second, two seconds, or any other such period of time). Alternative to adjusting the width W to detect a signal, the transmitting device (e.g., ICD system 30) may identify that PD 16 has not delivered therapy and in response increase the transmission rate of the signals in an attempt to increase the probability that the receiving device will receive a signal.

In some examples, processing circuitry 90 may terminate communication window 394 in response to receiving control signal 398 since communication circuitry 94 no longer needs to be powered. Processing circuitry 90 may also adjust the width X of communication windows based on when control signal 398 is received. For example, if control signal 398 is received very close to the expected time of the transmission window, the processing circuitry 90 may reduce the width W of communication windows to further conserve power. Conversely, if control signal 398 is received near the start or end of communication window 394, subsequent control signals might not be captured within the communication window. Therefore, processing circuitry 90 may lengthen the width W of the subsequent communication windows in order to ensure that transmitted signals are received. In addition, or alternative, to altering the width W of the communication windows, processing circuitry 90 may alter interval X to attempt to center control signals within the communication windows. Processing circuitry 90 may make these changes to width W and/or interval X based on single control signals or multiple control signals received over time by monitoring running averages, weighted averages, or any other metric for adjusting the communication schedule to align with the transmission schedule of the master device.

In some examples, the operations shown or described in flow diagrams may be performed in a different order or presented in a different sequence, but still be in accordance with one or more aspects of the present disclosure. Also, while certain operations may be presented in a particular sequence, in other examples, operations may be performed in parallel or substantially parallel, yet still be in accordance with one or more aspects of the present disclosure. Further, a process or technique in accordance with one or more aspects of the present disclosure may be implemented with less than the operations shown or described, and in other examples, such a process may be implemented with more than the operations shown or described.

Any suitable modifications may be made to the processes described herein and any suitable device, processing circuitry, therapy delivery circuitry, and/or electrodes may be used for performing the steps of the methods described herein. The steps the methods may be performed by any suitable number of devices. For example, a processing circuitry of one device may perform some of the steps while a therapy delivery circuitry and/or sensing circuitry of another device may perform other steps of the method, while communication circuitry may allow for communication needed for the processing circuitry to receive information from other devices. This coordination may be performed in any suitable manner according to particular needs.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to ICD system 30, PD 16, external device 21, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an application specific integrated circuit (ASIC), an electronic circuit, a processor (shared, dedicated, or group) and memory that execute one or more software or firmware programs, a combinational logic circuit, or other suitable components that provide the described functionality.

Such hardware, software, firmware may be implemented within the same device or within separate devices to support the various operations and functions described in this disclosure. For example, any of the techniques or processes described herein may be performed within one device or at least partially distributed amongst two or more devices, such as between ICD system 30, PD 16, and/or external device 21. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for delivering cardiac stimulation therapies as well as coordinating the operation of various devices within a patient. Any combination of the described operations or functions is contemplated. These and other examples may be within the scope of the following claims.

The invention claimed is:

1. A method comprising:
   initiating, by an implantable medical device, a communication window;
   responsive to initiating the communication window and during the communication window:
      turning on, by the implantable medical device, communication circuitry of the implantable medical device to receive signals from a second medical device, and
      wirelessly receiving information, via the communication circuitry, from the second medical device, wherein the communication window comprises one communication window of a plurality of communication windows, wherein each communication window is defined by a communication schedule that corresponds to a transmission schedule, wherein the transmission schedule defines a plurality of transmission windows in which the second medical device is configured to transmit the information, and wherein the information comprises information indicative of a timing of a cardiac event with respect to a timing of the communication window;
   turning off, by the implantable medical device, the communication circuitry at least between each communication window of the plurality of communication windows;
   scheduling, by the implantable medical device, delivery of a therapy according to the information; and
   delivering, by the implantable medical device, the therapy to a patient.

2. The method of claim 1,
   wherein the information comprises a control signal from the second medical device that defines a time at which the implantable medical device is to deliver the therapy,
   wherein scheduling delivery of the therapy comprises scheduling, by the implantable medical device, delivery of the therapy at the time according to the control signal, and
   wherein delivering the therapy comprises delivering, by the implantable medical device, the therapy at the time.

3. The method of claim 2, wherein the control signal indicates a delay period between receiving the control signal and the time at which the implantable medical device is to deliver the therapy.

4. The method of claim 2, further comprising, responsive to receiving the control signal, initiating, by the implantable medical device, a blanking window during which the implantable medical device does not initiate any communication windows of the plurality of communication windows.

5. The method of claim 4, further comprising:
determining an average time between a plurality of received control signals that includes the received control signal; and
adjusting, based on the average time, the duration of the blanking window.

6. The method of claim 4, further comprising:
determining that the blanking window has elapsed; and
responsive to determining that the blanking window has elapsed, initiating a next communication window according to the communication schedule.

7. The method of claim 1, wherein the implantable medical device is configured to determine a time to deliver the therapy based on the information related to the cardiac event that is indicative of the timing of the cardiac event with respect to the timing of the communication window.

8. The method of claim 1, wherein initiating the communication window comprises starting the communication window prior to an expected transmission window of the transmission schedule, the communication window continuing for a duration of time that includes the expected transmission window.

9. The method of claim 1, further comprising, responsive to receiving the information via the communication circuitry, terminating the communication window by disabling communication circuitry of the implantable medical device.

10. The method of claim 1, further comprising extending a duration of the communication window until the information is completely received.

11. The method of claim 1, further comprising, based on when the information is received, altering at least one of a starting time of a subsequent communication window or a window duration of the subsequent communication window to align the communication schedule and the transmission schedule to capture subsequent information from the second medical device.

12. The method of claim 11, wherein:
receiving the information comprises receiving the information within a predetermined percentage of one of a start or an end to the communication window; and
altering the window duration of the subsequent communication window comprises, responsive to receiving the information within the predetermined percentage of one of the start of the end of the communication window, lengthening the window duration of the subsequent communication window.

13. The method of claim 11, wherein:
receiving the information comprises receiving the control signal within a predetermined percentage of an expected time for receiving the information; and
altering the window duration of the subsequent communication window comprises, responsive to receiving the information within the predetermined percentage of the expected time for receiving the information, shortening the window duration of the subsequent communication window.

14. The method of claim 1, further comprising:
generating, based on when the information is received, a clock signal correction factor that corrects for the difference between when the information was received and an expected time for receiving the information was expected; and
applying the clock signal correction factor to a clock signal of the implantable medical device to temporally align the communication schedule with the transmission schedule.

15. The method of claim 1, wherein each communication window of the plurality of communication windows occurs at a predetermined rate.

16. The method of claim 15, wherein the predetermined rate corresponds to intervals from approximately 20 milliseconds (ms) to approximately 100 ms between adjacent transmission windows.

17. The method of claim 1, wherein the plurality of communication windows have an average duty cycle of less than two percent of the communication schedule.

18. The method of claim 1, wherein the therapy is a left ventricle pacing signal.

19. The method of claim 1, wherein the implantable medical device is configured to be implanted within a left ventricle of a heart of the patient.

20. The method of claim 1, wherein turning on the communication circuitry comprises turning on an amplifier of the communication circuitry.

21. An implantable medical device comprising:
communication circuitry configured to wirelessly receive information from a second medical device;
therapy delivery circuitry configured to deliver therapy to a patient; and
processing circuitry configured to:
initiate a communication window, wherein during the communication window the implantable medical device is configured to:
turn on the communication circuitry to receive signals from the second medical device;
wirelessly receive the information from the second medical device, wherein the communication window comprises one communication window of a plurality of communication windows, wherein each communication window is defined by a communication schedule that corresponds to a transmission schedule, wherein the transmission schedule defines a plurality of transmission windows in which the second medical device is configured to transmit the information, and wherein the information comprises information indicative of a timing of a cardiac event with respect to a timing of the communication window;
turn off the communication circuitry at least between each communication window of the plurality of communication windows;
schedule delivery of a therapy according to the information; and
control the therapy delivery circuitry to deliver the therapy to the patient.

22. The implantable medical device of claim 21, wherein the processing circuitry is further configured to extend a duration of the communication window until the information is completely received.

23. The implantable medical device of claim 21, wherein the processing circuitry is further configured to, based on when the information is received, alter at least one of a starting time of a subsequent communication window or a window duration of the subsequent communication window to align the communication schedule and the transmission schedule to capture subsequent information from the second medical device.

24. The implantable medical device of claim 23, wherein:
receiving the information comprises receiving the information within a predetermined percentage of one of a start or an end to the communication window; and
altering the window duration of the subsequent communication window comprises, responsive to receiving the information within the predetermined percentage of one of the start of the end of the communication window, lengthening the window duration of the subsequent communication window.

25. The implantable medical device of claim 21, wherein turning on the communication circuitry comprises turning on an amplifier of the communication circuitry.

\* \* \* \* \*